United States Patent
Kloss et al.

(10) Patent No.: US 11,155,542 B2
(45) Date of Patent: Oct. 26, 2021

(54) ANTIMICROBIAL COMPOUNDS, THEIR USE FOR THE TREATMENT OF MAMMALIAN INFECTIONS AND A NEW METABOLIC MECHANISM

(71) Applicants: Leibniz-Institut für Naturstoff-Forschung und Infektionsbiologie E.V. Hans-Knöll Institut (HKI), Jena (DE); Klinikum der Universität München, Munich (DE); University of Notre Dame du Lac, Office of Technology Transfer, South Bend, IN (US)

(72) Inventors: Florian Kloss, Jena (DE); Sebastian Schieferdecker, Jena (DE); Axel Brakhage, Weimar (DE); Julia Dreisbach, Munich (DE); Marvin J. Miller, South Bend, IN (US); Ute Mollmann, Jena (DE); Kamil Philip Wojtas, Weimar (DE)

(73) Assignees: University of Notre Dame Du Lac, South Bend, IN (US); Leibniz-Institut fur Naturstoff-Forschung und Infektionsbiologie E.V. Hans-Knoll Institut (HKI); Klinikum der Universitat Munchen

( * ) Notice: Subject to any disclaimer, the term of this patent is extended or adjusted under 35 U.S.C. 154(b) by 187 days.

(21) Appl. No.: 16/335,384

(22) PCT Filed: Sep. 21, 2017

(86) PCT No.: PCT/EP2017/073935
§ 371 (c)(1),
(2) Date: Mar. 21, 2019

(87) PCT Pub. No.: WO2018/055048
PCT Pub. Date: Mar. 29, 2018

(65) Prior Publication Data
US 2020/0407351 A1    Dec. 31, 2020

(30) Foreign Application Priority Data
Sep. 22, 2016 (EP) .................... 16190199

(51) Int. Cl.
*C07D 513/04* (2006.01)
*A61P 31/04* (2006.01)
(Continued)

(52) U.S. Cl.
CPC ......... *C07D 417/04* (2013.01); *C07D 513/04* (2013.01)

(58) Field of Classification Search
CPC ......... C07D 513/04; A61P 31/04; A61P 31/06
See application file for complete search history.

(56) References Cited

U.S. PATENT DOCUMENTS

2015/0353572 A1    12/2015    Miller et al.

FOREIGN PATENT DOCUMENTS

DE    10 2014 012546 A1    9/2014
EP         2719691 A1    4/2014
(Continued)

OTHER PUBLICATIONS

Kloss et al. Angewandte Chemie International Edition / vol. 56, Issue 8,20 pages. (Year: 2017).*
Gao, Chao et al: "Synthesis and structure-activity relationships evaluation of benzothiazinone derivatives as potential antitubercular agents", Bioorganic & Medicinal Chemistry Letters, vol. 23, No. 17, 2013,—2013, pp. 4919-4922.
Karoli, Tomislov et al: "Identification of 8-12 Antitubercular Benzothiazinone Compounds by Ligand-Based Design", Journal of Medicinal Chemistry, vol. 55, No. 17, Sep. 3, 2012 (Sep. 13, 2012), pp. 7940-7944.
(Continued)

*Primary Examiner* — Emily A Bernhardt
(74) *Attorney, Agent, or Firm* — Adsero IP

(57) ABSTRACT

The present invention relates to the general field of treatment of infectious diseases of mammals (humans and animals) caused by bacteria, in particular to the treatment of diseases like tuberculosis (TB), Buruli ulcer and leprosy caused by mycobacteria. The invention aims at the generation of a new series of benzothiazinone compounds having the potential to overcome the above mentioned problems. In a preferred embodiment the invention is concerned with compounds of the general formula (I)

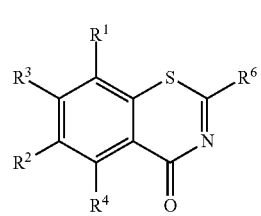

wherein
$R^1$ represents $NO_2$,
$R^2$ represents $CF_3$,
at least one of the substituents $R^3$ and $R^4$ is OH, $SR^{14}$, $NHR^{15}$, CN, $N_3$, a saturated or unsaturated, optionally halogenated, linear or branched aliphatic radical having 1-4 carbon atoms, linear or branched $C_1$-$C_4$ alkoxy, $C_1$-$C_4$ acyl, and the other of $R^3$ and $R^4$ may in addition be hydrogen,
$R^6$ represents a 2-methyl-1,4-dioxa-8-azaspiro[4.5]decan-8-yl or a 4-(cyclo-hexylmethyl)piperazin-1-yl group and
$R^{14}$ and $R^{15}$ independently of each other are hydrogen or a $C_1$-$C_4$ alkyl group and/or a pharmaceutically acceptable salt thereof.

7 Claims, 4 Drawing Sheets

(51) Int. Cl.
*A61P 31/06* (2006.01)
*C07D 417/04* (2006.01)

(56) References Cited

FOREIGN PATENT DOCUMENTS

WO WO 2007/134625 A1 11/2007
WO WO 2012/066518 A1 5/2012
WO WO 2013/185507 A1 12/2013

OTHER PUBLICATIONS

Kloss, Florian et al.: "In-vivo Dearomatisierung des potenten Antituberkulose-Wirkstoffs BTZ043 durch Bildung eines Meisenheimer-Komplexes", Angewandte Chemie, vol. 129, No. 8, 18. Jan. 2017 (Jan. 18, 2017), pp. 2220-2225.

Lipunova G. N. et al: "Fluorine-containing heterocycles: XVII. (Tetrafluorobrnzoyl)thioureas in the synthesis of fluorine-containing azaheterocycles", Russian Journal of Organic Chemistry., vol. 44, No. 5, May 1, 2008 (May 1, 2008), pp. 741-749.

Makarov, V. et al: "Towards a new combination therapy for tuberculosis with next generation benzothiazinones", EMBO Molecular Medicine, vol. 6, No. 3, Mar. 1, 2014, pp. 372-383.

Nosova, É. V. et al: "Synthesis and Tuberculostatic Activity of Fluorine—Containing Derivatives of Quinolone, Quinazolinone, and Benzothiazinone" (Translated from Khimiko-Farmatsevticheskii), Retrieved from the Internet: URL:http://rd.springer.com/content/pdf/10. 1007/511094-008-0083-0.pdf.

* cited by examiner

ANTIMICROBIAL COMPOUNDS, THEIR USE FOR THE TREATMENT OF MAMMALIAN INFECTIONS AND A NEW METABOLIC MECHANISM

CROSS-REFERENCE TO RELATED APPLICATIONS

This application claims priority to and is a 35 U.S.C. § 371 national phase application of PCT/EP2017/073935 (WO 2018/055048), filed on Sep. 21, 2017 entitled "New antimicrobial compounds, their use for the treatment of mammalian infections and a new metabolic mechanism," which application claims priority to and the benefit of EP Application No. 16190199.6, filed Sep. 22, 2016, the contents of which are incorporated herein by reference in their entirety.

TECHNICAL FIELD

The present invention relates to the general field of treatment of infectious diseases of mammals (humans and animals) caused by bacteria, in particular to the prophylactic or therapeutic treatment of diseases like tuberculosis (TB), Buruli ulcer and leprosy caused by mycobacteria.

In particular the invention reports about recent in vivo metabolic studies of known anti-tuberculosis compounds, the results achieved thereby and about a new series of benzothiazinone compounds that have the potential to improve the bioactivity and in vivo metabolic stability compared to known compounds.

BACKGROUND OF THE INVENTION

Infectious Diseases like tuberculosis, leprosy and Buruli ulcer that result from infections with mycobacteria belong to the most challenging threats to human health in terms of disease burden and mortality. As a consequence there is an urgent need for new drugs with improved bioactivity or improved metabolic stability, especially to overcome drug resistance and to overcome the known dramatic side effects of the available drugs.

Benzothiazinones and their use as antimicrobial agents, especially against mycobacteria, are generally known. (S)-2-(2-methyl-1,4-dioxa-8-azaspiro[4.5] decan-8-yl)-8-nitro-6-(trifluoro-methyl)-4H-benzo[e][1,3]thiazin-4-one (BTZ043) and the related 2-[4-(cyclohexylmethyl)piperazin-1-yl]-8-nitro-6-(trifluoromethyl)-4H-1,3-benzothiazin-4-one (PBTZ169) are described in WO 2007/134625 and WO2012/066518. Both compounds are extraordinarily potent anti-tuberculosis agents that are undergoing extensive studies for possible development.

SUMMARY OF THE INVENTION

In view of the above background, it is highly desirable to develop new compounds that do not only provide high antibacterial activity against mycobacteria but also display alternative or even improved properties, such as safety, metabolic stability and a good ADME profile, compared to previously described compounds.

The present invention aims at the generation of a new series of benzothiazinone compounds having the potential to overcome the above mentioned problems.

Recent in vivo studies with benzothiazinones that are reported as part of the present invention revealed a new and fully unprecedented reduction pathway involving Meisenheimer complexes of BTZ043 and PBTZ169. This reduction pathway has been verified by chemical studies that allowed a detailed characterization of the Meisenheimer complex and its subsequent chemistry.

Combination of these in vivo studies and chemical studies with LC-MS physiochemical characterization and assay development also provided the basis for rational lead optimization of this promising class of anti-tuberculosis agents. In particular, it was found that the in vivo metabolism of nitro-substituted benzothiazinone compounds involves a dearomatization of the nitrobenzothiazinone moiety. Replacing one or both hydrogen atoms in positions $R^3$ and $R^4$ in the following formula (I) by a larger substituent allows changing the critical metabolism of these benzothiazinones and thus a rational access to further improved anti-mycobacterial compounds.

In a preferred embodiment the present invention is, thus, concerned with a compound of formula (I)

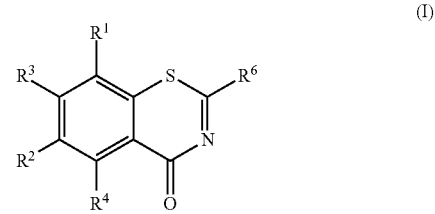

(I)

wherein
$R^1$ represents $NO_2$,
$R^2$ represents $CF_3$,
at least one of the substituents $R^3$ and $R^4$ is OH, $SR^{14}$, $NHR^{15}$, CN, $N_3$, a saturated or unsaturated, optionally halogenated, linear or branched aliphatic radical having 1-4 carbon atoms, linear or branched $C_1$-$C_4$ alkoxy, $C_1$-$C_4$ acyl, and the other of $R^3$ and $R^4$ may in addition be hydrogen,
$R^6$ represents a 2-methyl-1,4-dioxa-8-azaspiro[4.5]decan-8-yl or a 4-(cyclo-hexylmethyl)piperazin-1-yl group and
$R^{14}$ and $R^{15}$ independently of each other are hydrogen or a $C_1$-$C_4$ alkyl group and/or a pharmaceutically acceptable salt thereof.

In one embodiment in the above formula (I) according to embodiment [1] both $R^3$ and $R^4$ are as defined above, and are different from hydrogen. In another embodiment of the invention, $R^3$ is hydrogen, and $R^4$ is as defined above. In a further embodiment of the invention $R^4$ is hydrogen, and $R^3$ is as defined above.

The novel benzothiazinone compounds of the invention and/or their pharmaceutically acceptable salts are useful for the therapeutic treatment of a disease. Preferably, the disease is selected from the group comprising tuberculosis, leprosy or Buruli ulcer.

d) HPLC chromatogram section (254 nm UV-traces) of a blood plasma sample of a BTZ043-treated minipig (top) compared to the product mixture obtained through NaBH$_4$ mediated reduction of BTZ043 (bottom).

Figure 2:
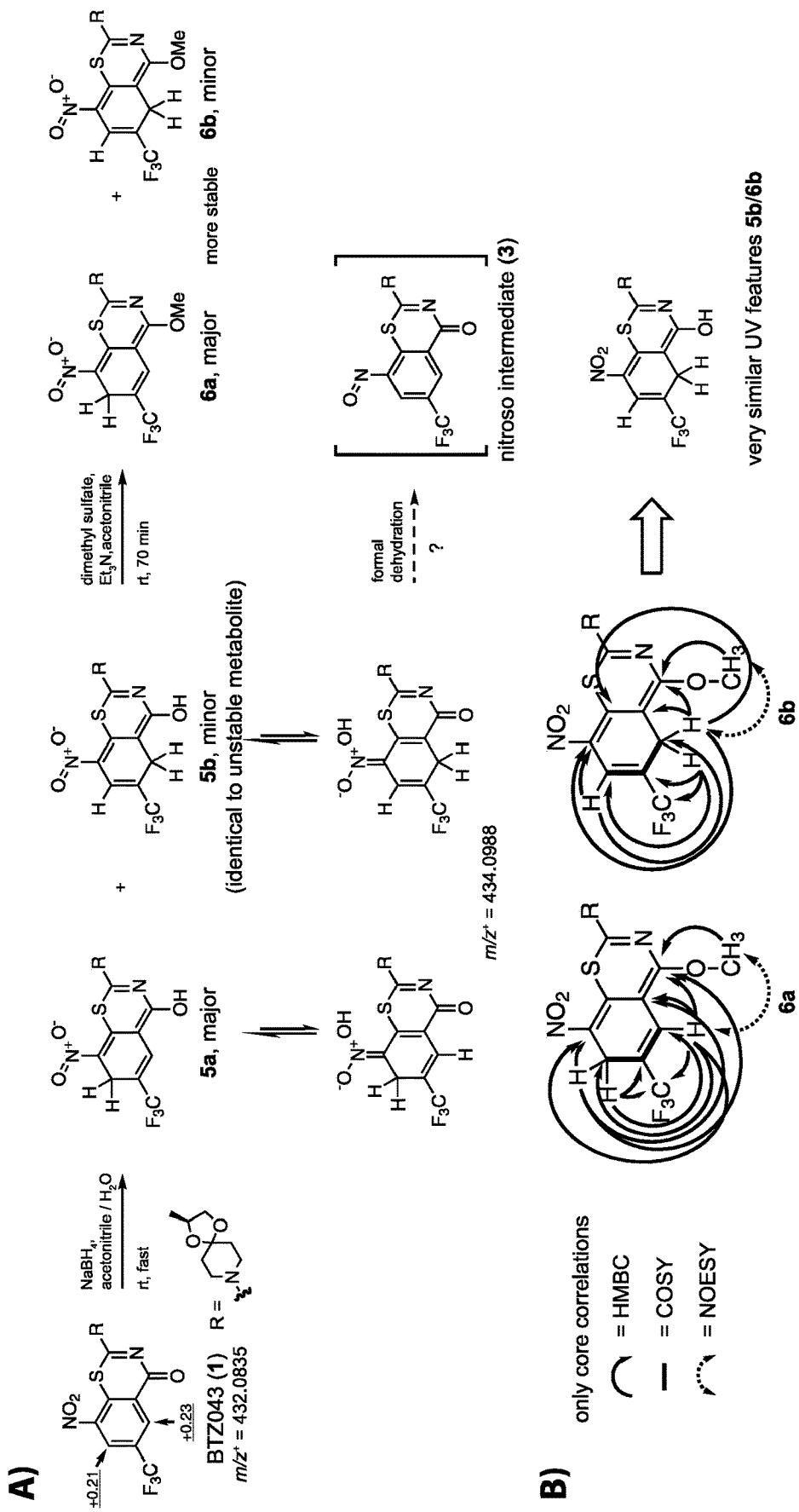

FIG. 2a)-b):
a) Schematic representation of the reduction and methylation step
b) structures of the 6a/b and 5b and characteristic COSY, NOESY and HMBC couplings of 6a/b.

Figure 3:
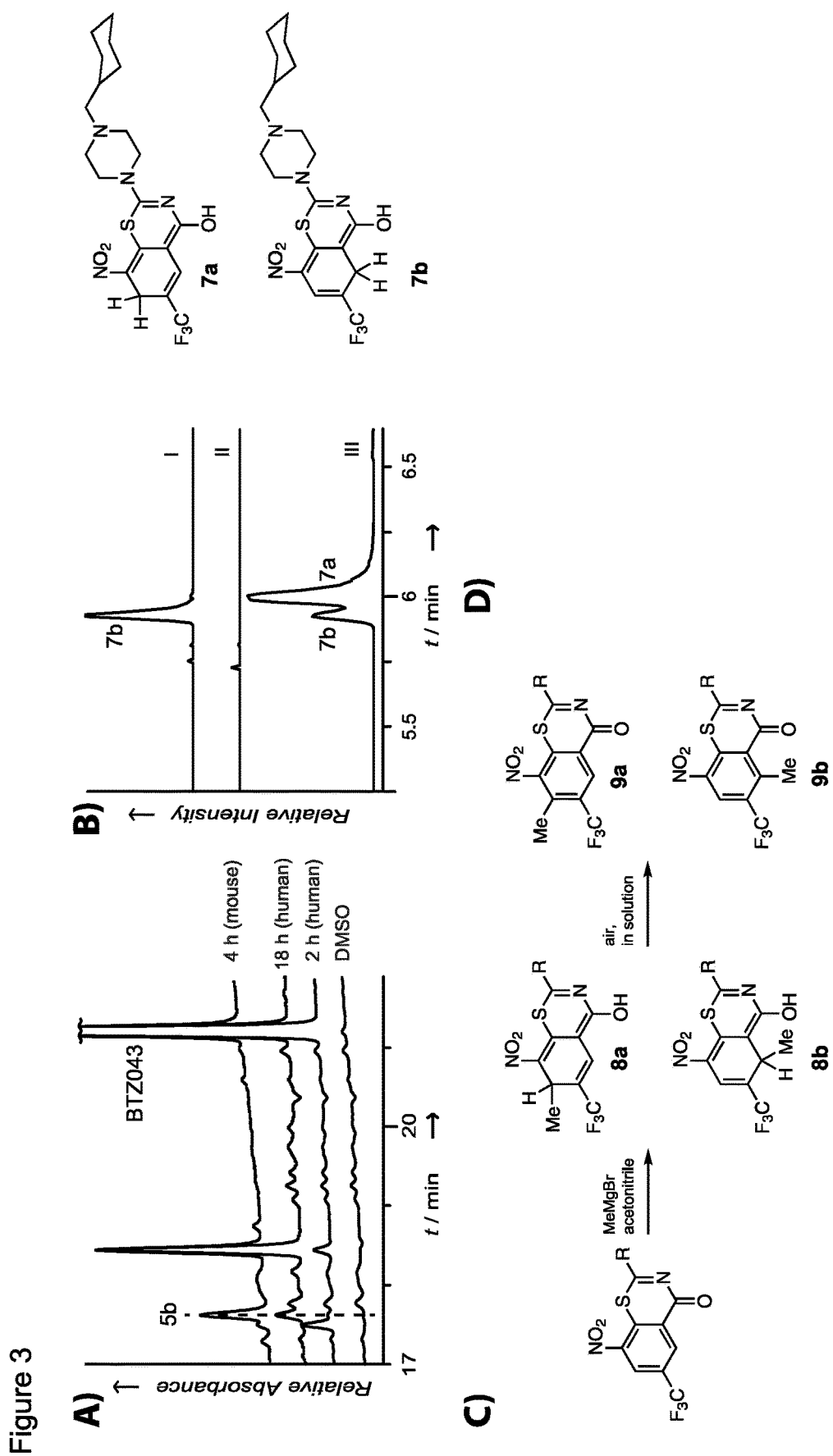

FIG. 3a)-d):
a) HPLC profile section (254 nm traces) of plasma samples, gained after in vitro incubation of fresh whole blood with BTZ043 and DMSO (control with human blood); identity of 5b has unequivocally been assured by UV-characteristics and retention time;
b) Extracted ion chromatograms (HPLC-HRMS, positive mode) at m/z=459.1649-459.1695 (corr. 7b [PBTZ169+2H+H]+) of I: plasma samples, gained after in vitro incubation of fresh whole blood with PBTZ169; II: plasma samples, gained after in vitro incubation of fresh whole blood with BTZ043 (negative control); III: reference mixture prepared by reduction of PBTZ169 with NaBH$_4$ in acetonitrile/water; the regiochemistry of 7a/7b was proposed in analogy to 5a/b;
c) Schematic representation of the Me-Grignard reaction with BTZ043
d) Normalized extracted ion chromatograms (HPLC-HRMS, positive mode) of a plasma sample gained after in vitro incubation of fresh whole blood with I: BTZ043 (positive control) at m/z=434.0970-434.1014 (corr. 5b [BTZ043+2H+H]+); controls: reference mixture prepared by reduction of II: 9a and III: 9b with NaBH$_4$ in acetonitrile/water; regiochemistry was not assigned.

Figure 4:
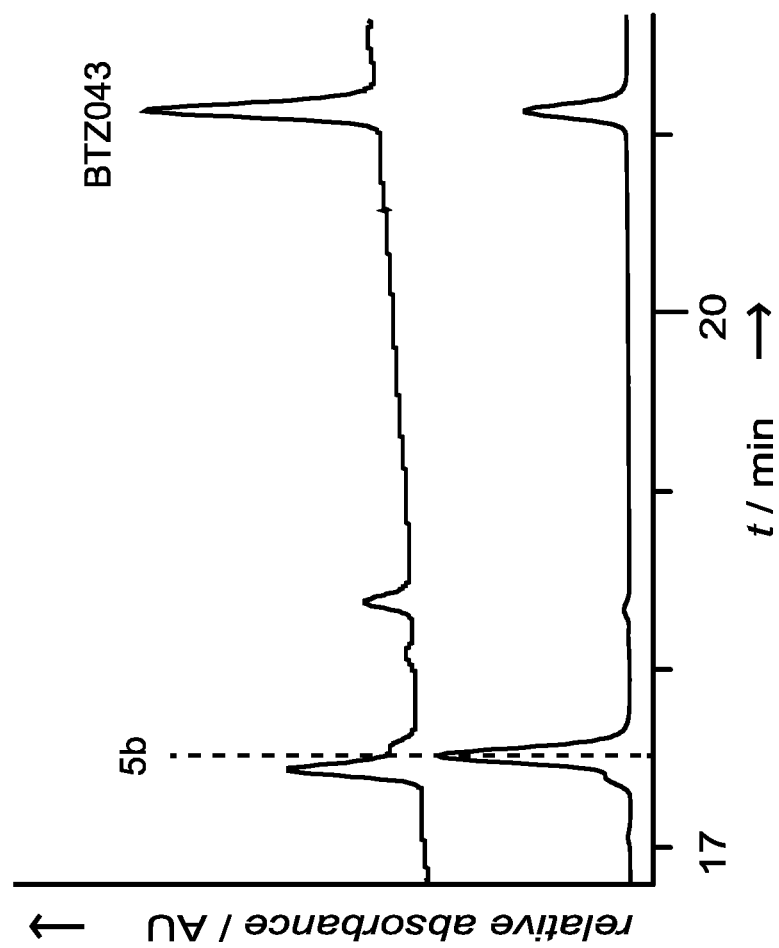

FIG. 4:
HPLC profile sections (254 nm traces) of the synthesized 5b reference compound (bottom) and the supernatant from a yeast cell suspension incubated with BTZ043 anaerobically for 15 min (top); identity of 5b has unequivocally been assured by UV-characteristics and retention time.

DETAILED DESCRIPTION OF THE INVENTION

The present invention discloses the results of recent in vivo studies regarding the use of the known benzothiazinone compounds BTZ043 and PBTZ169 that revealed a new and fully unprecedented reduction pathway involving Meisenheimer complexes of the two compounds. The reduction has been verified by chemical studies that allowed complete characterization of the Meisenheimer complex and its subsequent chemistry by use of a combination of the in vivo studies and chemical studies with LC-MS physiochemical characterization and assay development.

BTZ043, having the chemical structure (S)-2-(2-methyl-1,4-dioxa-8-azaspiro[4.5]decan-8-yl)-8-nitro-6-(trifluoromethyl)-4H-1,3-benzothiazin-4-one, (1), and the related compound PBTZ169, having the chemical structure 2-[4-[cyclohexylmethyl]piperazin-1-yl]-8-nitro-6-(trifluoromethyl)-4H-1,3-benzo-thiazin-4-one, (2), are extraordinarily potent antituberculosis agents that are undergoing extensive studies for possible development (Makarov et al. Benzothiazinones Kill *Mycobacterium tuberculosis* by Blocking Arabinan Synthesis. Science 324, 801-804 (2009).

Figure 1:
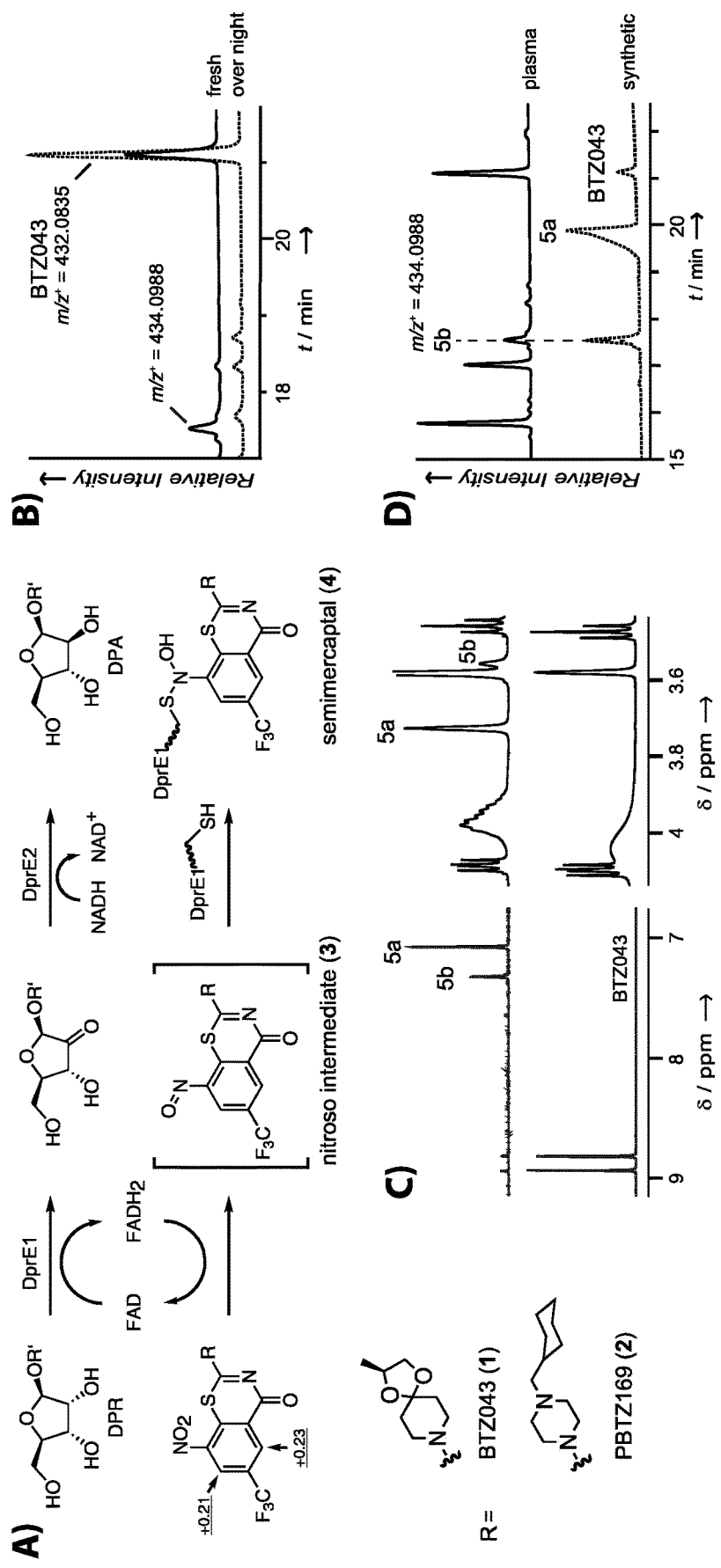
FIG. 1a)-d):
a) Discloses the molecular mechanism of action of nitrobenzothiazinones in general;
b) Representative HPLC chromatogram section (254 nm UV-traces) of blood plasma samples of BTZ043-treated minipigs direct (top) and several hours (bottom) after sample preparation;
c) Characteristic chemical shift regions of the product mixture obtained through $NaBH_4$ mediated reduction of BTZ043.

As shown in FIG. 1, BTZ043, related benzothazinones and simplified analogs, (Ref. 1) are prodrugs in which the nitro substituent is reduced to a transient nitroso moiety, (3), that then reacts with an essential cysteine residue of decaprenylphosphoryl-β-D-ribose 2' oxidase (DprE1) of *Mycobacterium tuberculosis* (Mtb) to give a semimercaptal (4). The DprE1 enzyme is required for arabinan biosynthesis, an essential process for the cell wall assembly of mycobacteria (Ref. 2), and formation of the covalent adduct, (4), results in inhibition and loss of viability of *Mycobacterium tuberculosis*. Details of the key reduction chemistry are thus of considerable interest. It has previously been reported that nucleophiles, including thiolates that mimic the cysteine, undergo classical cine additions (Ref. 3) (Von Richter reactions, Ref. 4) to the nitroaromatic core of BTZ043 and analogs with concomitant reduction of the nitro group to the transient and reactive nitroso intermediate (Ref. 5). The regioselective electrophilicity of the nitroaromatic core was consistent with Mulliken charge calculations that indicated significant positive character ortho and para to the nitro group (see structure 1).

We found that BTZ043 is also metabolically reduced in vivo by hydride to form transient, but isolable, Meisenheimer complexes that are then readily re-oxidized to the parent compound. The reduction can also be performed chemically to provide ample quantities of the Meisenheimer complexes for full physiochemical characterization and confirmation of subsequent chemical transformations. Elucidation of this process clarified observations of variable drug concentrations during in vivo experiments while also providing insight into novel in vivo prodrug generation and, ultimately, new anti-mycobacterial drugs. The results have significant implications that will be important to consider during continuing development of this important class of anti-tuberculosis agents.

The low nanomolar in vitro anti-tuberculosis activity of BTZ043 prompted very early in vivo studies. When some plasma samples were repeatedly analyzed for drug exposure after storage at room temperature the analyte concentration and bioactivity of the respective plasma samples seemed to increase significantly.

Several years after this incident, drug exposure values in PK studies were again characterized by exceptionally high deviations and enigmatic increases of the determined concentrations of BTZ043 over time (see FIG. 1b).

Interestingly, this observation was not made when blank plasma from untreated animals was spiked with BTZ043. In the spiked samples, the peak areas remained completely unchanged over time. It was therefore reasoned, that a possible explanation of this phenomenon would involve a yet unknown metabolite that was either thermally or oxidatively unstable when exposed to air. However, earlier standardized in vitro metabolism assays (microsomes and hepatocytes) did not identify metabolites that would help formulate a conclusive chemical hypothesis.

In order to reveal potentially overlooked metabolites, additional metabolic studies of BTZ043 were performed that incorporated careful analysis of highly resolved HPLC chromatograms of plasma samples after different incubation times at room temperature. To ensure maximum stability of the chromatographic conditions, all solvents were carefully degassed through vacuum treatment and/or sparging with nitrogen. Indeed, under these more rigorous conditions, it was found that while the integrated area due to the parent drug increased over time, an earlier eluting peak with a very unusual UV spectrum was initially noted but found to disappear over time (FIG. 1b). The concomitant drastic increase of the BTZ043 peak area (in some samples >100%) emphasized the significance of this transient metabolite. HRMS analysis suggested that this newly detected compound (m/z$^+$=434.0988, $C_{17}H_{19}F_3O_5N_3S^+$) contained only two hydrogen atoms more than BTZ043 itself (m/z$^+$=432.0835, $C_{17}H_{17}F_3N_3O_5S^+$). It was suspected that this metabolite could be formed through an enzymatic reduction of BTZ043 and that it is unstable towards oxygen from air.

Due to its chemical instability and the limited availability of material from plasma, alternative methods were sought to obtain ample amounts for detailed studies. Based on its molecular mass, it was anticipated that the new compound might be available by chemical reduction of BTZ043. Furthermore, based on the cine addition chemistry reported earlier, it was anticipated that simple chemical hydride sources could also initiate the reduction process. Indeed, treatment of BTZ043 with $NaBH_4$ in various solvents resulted in immediate formation of a persistent bright orange/red solution. LC/MS of an aliquot of the reaction mixture taken 30 seconds after the addition of the hydride revealed generation of a compound mixture containing a peak with retention time, distinct UV spectrum and mass identical to the previously detected metabolite. Addition of excess $NaBH_4$ drove the reaction to completion.

Interestingly, the same reduced metabolite was not produced when BTZ043 was treated with a variety of other reducing conditions including Pd/C ($H_2$), Pt/C ($H_2$)), electrochemical reduction (Pt/Pt), $Zn/NH_4Cl_{aq.}$, $BH_3$-adducts, triethylsilane, sulfur dioxide, sodium dithionite, Hantzsch ester (Ref. 8) and NADH. Reactions with milder boron based hydrides $NaBH(OAc)_3$ and $NaBH_3CN$ were ineffective and resulted in complete recovery of the starting BTZ043. Subsequent analysis by $^1H$ NMR spectroscopy revealed that the reduced product formed actually was a mixture of two major components (FIG. 1c) which co-eluted under the neutral chromatographic conditions initially employed. When HPLC was performed at acidic pH (0.1% trifluoroacetic acid (TFA)), both compounds could be separated. The two compounds had substantially different UV spectra but the same mass peak (m/z$^+$=434.0988) suggesting that they were isomers. The reduced compounds could be isolated by either of two methods. Removal of the reaction solvent, followed by preparative HPLC and lyophilization gave a brilliant orange red solid, which upon re-analysis by LC/MS and detailed NMR studies was confirmed to be a mixture of the same reduction products. Alternatively, upon acidification of the reaction mixture with TFA, a deep red pigment precipitated which could be washed, collected by centrifugation and vacuum dried (FIG. 2a). While the solid proved to be quite stable at room temperature and even atmospheric oxygen for short periods, when the acidified reaction mixture was allowed to stand or if the isolated solid was dissolved and stored in non-degassed solution, the reduced material readily re-oxidized to BTZ043.

Detailed LC/MS experiments using this chemically generated reaction product mixture as reference material showed that minor isomer (5b) was in fact identical to the unknown metabolite observed in plasma samples from minipigs which had received oral doses of BTZ043 while the main constituent (5a) was completely absent in the plasma samples (see FIG. 1d).

Preliminary NMR studies of the mixture of reduction products indicated loss of the characteristic aromatic proton signals for BTZ043 (1) and appearance of additional upfield signals. This, along with the rapid formation of the red/orange color during the reduction, and the previous observations of cine addition chemistry of nucleophiles to BTZ043, suggested that hydride might have added to form a transient, but detectable Meisenheimer complex.

Since the acidic HPLC conditions required to separate the isomeric reduction products also promoted rapid re-oxidation during handling, it was sought to generate more stable, isolable derivatives for more detailed structural confirmation.

It was anticipated that the de-aromatized reduced products should be susceptible to reactions with electrophiles that might provide derivatives suitable for detailed characterization. Indeed, reaction of the reduction product mixture with dimethyl sulfate afforded two new less polar products (6a, b) with separate UV spectra that were nearly identical to the metabolite (5b) and its isomer (5a) (FIG. 2a).

The newly identified structures 5a and 5b as well as 6a and 6b, thus, form part of the invention.

Both compounds proved to be sufficiently soluble and stable at room temperature to allow for their isolation on multi milligram scale by preparative HPLC and their full characterization by 1D and 2D NMR. Consistent with generation of a Meisenheimer complex each isomer (6a/b) had only one low field proton (7.0 and 7.3 ppm, respectively) and a new upfield signal (3.7 and 3.5 ppm, respectively) that was later assigned to be a methylene group by DEPT135 measurements. This data unequivocally showed that the reduction of BTZ043 occurs at the aromatic core and the two products (6a/b corresponding to 5a/b) are regioisomers of a hydride Meisenheimer complex (FIG. 2a). Meisenheimer complexes are known, but often are very unstable intermediates in nucleophilic substitution reactions of electron poor aromatic systems and rare examples have been identified in biological systems, such as in the biodegradation of explosives like TNT by *Yarrowia lipolytica*.

However, to our knowledge transformations to afford Meisenheimer complexes in vivo have not been described for any drug or drug candidate. The installation of the methyl group in 6a/b also allowed assignment of the regiochemistry of both isomers through a combination of NOESY and HMBC coupling studies (FIG. 2b). Although the chemical hydride reduction produced two isomeric products, the fact, that only 5b was observed in vivo suggested that an enzymatic process might be involved in generation of the metabolite, which also might then serve as a direct precursor for the active nitroso analogue (FIG. 2a). Thus, we screened biological materials for their ability to transform BTZ043 to 5b.

Consistent with the in vitro metabolism experiments, 5b was not able to be detected in microsomal degradation assays, not even under anaerobic conditions and in the presence of large excesses of added NADH. Also exposure to cell lines (K562, leukemia cell line) produced no traces of 5b (data not shown) when incubated with BTZ043 at 5 µg·mL$^{-1}$. However, HPLC analysis of fresh whole human blood exposed to BTZ043, revealed transformation of BTZ043 to 5b after several hours (see FIG. 3a). In contrast, no production of 5b was found in freshly prepared plasma (data not shown).

This experiment not only demonstrated that blood cells are capable of transforming nitrobenzothiazinones to the corresponding Meisenheimer complexes, but that formation of 5b is most likely relevant in humans as well.

This knowledge will be of tremendous importance for method development and sample handling when nitrobenzothiazinones enter clinical trials. To increase the reproducibility of the assay, we also investigated mouse blood from C57BL/6J mice for its metabolic capabilities and again found production of 5b (FIG. 3a). Further studies with plasma samples of minipigs and rats which received oral doses of BTZ043 produced similar results and suggest that the presumed reductive enzyme is abundant in mammals. Since PBTZ169 has the same electronically reactive core as BTZ043 we subjected it to similar chemical and blood-induced reduction studies. As expected, HPLC-HRMS analyses of the reactions indicate that PBTZ169 also does undergo comparable reduction to the corresponding Meisenheimer complex (7b) with the same regioselectivity as observed with BTZ043 (FIG. 3b). This again emphasizes the impact of this chemistry among these important nitrobenzothiazinone anti-tuberculosis agents. The demonstration of blood-induced reduction will allow metabolic investigations of nitrobenzothiazinone libraries for formation of the corresponding Meisenheimer complexes.

The fact that bioreduction of BTZ043 and PBTZ169 each produced single regioisomeric reduction products (i.e., 5b) provided opportunities for lead optimization and potential suppression of metabolism through installation of substituents at the 5-position of the benzothiazinone core. Binding models of benzothiazinones and DprE1 also indicated some flexibility at this position.

While preparation of 5-substituted benzothiazinones could be accomplished by modifying the BTZ043 synthetic route, inspired by the results of the hydride studies, we considered reactions with other nucleophiles in order to obtain substituted benzothiazinones in one step. As indicated, we previously reported that nucleophiles, including thiolates and cyanide undergo classical cine additions (Von Richter reactions) to the nitroaromatic core of BTZ043 and analogs.

It also could be shown that BTZ043 reacts readily with MeMgBr or (Me)$_2$Zn to afford the Me-BTZ Meisenheimer complexes (8a/b) that slowly oxidized to give a regioisomeric mixture of 9a/b. The isomers were separated by preparative HPLC and fully characterized.

Thus, also the new structures 8a/b and 9a/b form part of the invention.

The separate compounds were carefully studied for their metabolic behavior in the blood assay. In accord with the above hypothesis, the reduced form of isomer 9b could only be detected in trace amounts in the metabolic assay as shown by HPLC-HRMS analysis, but interestingly, also 9a formed only fairly detectable amounts of the Meisenheimer complex in vitro.

Motivated by these results, further derivatives of 1 and 2 were synthesized bearing methyl, ethyl, cyclopropyl, ethynyl and nitrile residues through a similar nucleophilic approach, while the corresponding Meisenheimer complex intermediates were oxidized through addition of 2,3-dichloro-5,6-dicyano-1,4-benzoquinone (DDQ). The new derivatives showed low cytotoxicities (HeLa), drastically reduced tendencies to form Meisenheimer complexes (relative hydride Meisenheimer complex (MHC) formation) in the blood assay and good to excellent antimycobacterial activities (Table 1). Best potencies against Mtb strain H37Rv and a poly drug resistant strain were observed for the 5-methyl derivatives of 1 and 2.

These results illustrate that the metabolic tendency to form Meisenheimer complexes of benzothiazinones can be tuned through installation of substituents in 5- and 7-position of the benzothiazinone core and set the stage for further targeted metabolically driven in depth structure-activity studies.

CONCLUSIONS

Thus, it could be demonstrated that unstable drug exposure in pharmacokinetic studies of benzothiazinones (BTZ043, PBTZ169) are a result of a yet overlooked metabolic transformation yielding Meisenheimer complexes. Those metabolites are oxygen sensitive and readily reconvert to the parent drug. Despite their unstability towards oxygen, significant quantities of the Meisenheimer complex 5b were detected as a single regioisomer in plasma samples of minipigs and rats which received BTZ043 orally.

To provide authentic reference material, a one-step synthetic approach was found in which sodium borohydride can be used to afford regioisomeric mixtures of the Meisenheimer complexes which were separable by HPLC.

Eventually, a method to stabilize these compounds through methylation was found, which was an important requirement to fully elucidate their structures and to assign their regiochemistry by NMR. To allow for the screening of other compounds which may also be prone to this metabolic transformation, a very simple, HPLC-HRMS based whole blood assay was designed and found that other benzothiazinones (e.g. PBTZ169) can also be transformed in the same way.

Finally, the high regioselectivity of the hydride attack in vivo prompted options for lead optimization, while a highly flexible approach was found to incorporate substituents at the benzothiazinone core in a one step strategy through nucleophilic attack.

It could be shown that the tendency to form Meisenheimer complexes in vitro can be controlled through the installation of these substituents.

As nitro compounds are quite prevalent among tuberculosis therapeutics there is a clear need to consider this type of metabolic transformations very early in the development as it may have significant implications for all downstream procedures, including bioanalytical quantification, toxicity assessment or simply the proper handling of biological material.

Particularly in lung tuberculosis treatment, liberation of BTZ043 through oxidation of the prodrug 5b in the lung signalizes an entirely new concept for targeted local antibiosis. Moreover, it is very likely to encounter similar transformations in other TB-development programs as the powerful benzothiazinone scaffold (see also PBTZ169, (2)) appears to be generally prone to this type of reduction chemistry.

[1] The present invention therefore also includes new compounds of formula

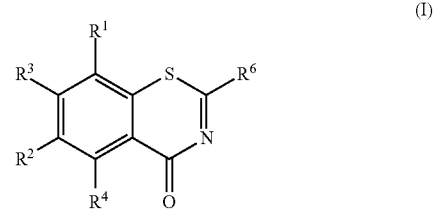

(I)

wherein
$R^1$ represents $NO_2$,
$R^2$ represents $CF_3$,
at least one of the substituents $R^3$ and $R^4$ is OH, $SR^{14}$, $NHR^{15}$, CN, $N_3$, a saturated or unsaturated, optionally halogenated, linear or branched aliphatic radical having 1-4 carbon atoms, linear or branched $C_1$-$C_4$ alkoxy, $C_1$-$C_4$ acyl, and the other of $R^3$ and $R^4$ may in addition be hydrogen.
$R^6$ represents a 2-methyl-1,4-dioxa-8-azaspiro[4.5]decan-8-yl or a 4-(cyclo-hexylmethyl)piperazin-1-yl group and $R^{14}$ and $R^{15}$ independently of each other are hydrogen or a $C_1$-$C_4$ alkyl group $R^{14}$, $R^{15}$ represent independently of each other hydrogen or a $C_1$-$C_4$ alkyl group and/or a pharmaceutically acceptable salt thereof.

The different substituents of a compound of formula (I) are defined as follows:

The halogen atom is a fluorine atom, a chlorine atom, a bromine atom or an iodine atom.

The aliphatic radical is a linear or branched $C_1$-$C_6$ alkyl, $C_2$-$C_6$ alkenyl, $C_2$-$C_6$ alkinyl or a $C_3$-$C_6$ cycloalkyl radical.

The $C_1$-$C_6$ alkyl is a linear or branched alkyl, and includes methyl, ethyl, isopropyl, butyl, isobutyl, secondary butyl, tertiary butyl, pentyl, 3-methylbutyl, neopentyl, hexyl, 2-ethylbutyl.

The $C_1$-$C_4$ alkyl is a linear or branched alkyl, and includes methyl, ethyl, isopropyl, butyl, isobutyl, a secondary or a tertiary butyl.

The $C_2$-$C_6$ alkenyl is a linear or branched alkenyl, and includes vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl.

The $C_2$-$C_6$ alkinyl is a linear or branched alkinyl, and includes ethinyl, propinyl, butinyl, pentinyl, hexinyl.

The $C_3$-$C_6$ cycloalkyl is cyclopropyl, cyclobutyl, cyclopentyl, cyclohexyl.

The aliphatic radical may be substituted by fluorine, chlorine, bromine or iodine.

The $C_1$-$C_4$ alkoxy is a linear or branched alkoxy, and methoxy, ethoxy, propoxy or isopropoxy, butoxy or isobutoxy.

The $C_1$-$C_4$ acyl includes a formyl, acetyl, propionyl and butyryl group.

The new compounds of formula (I) can be synthesized according to methods that known in the art.

Preferably, in the above formula (I) both $R^3$ and $R^4$ are as defined above, and are both different from hydrogen. In another embodiment of the invention, $R^3$ is hydrogen, and $R^4$ is as defined above. In a further embodiment of the invention $R^4$ is hydrogen, and $R^3$ is as defined above.

[2] A preferred embodiment is a compound of formula (I) according to [1] selected from the group consisting of (S)-7-Methyl-2-(2-methyl-1,4-dioxa-8-azaspiro[4.5]decan-8-yl)-8-nitro-6-(trifluoromethyl)-4H-1,3-benzothiazin-4-one (9a)

(S)-5-Methyl-2-(2-methyl-1,4-dioxa-8-azaspiro[4.5]decan-8-yl)-8-nitro-6-(trifluoromethyl)-4H-1,3-benzothiazin-4-one (9b)

(S)-5-Ethyl-2-(2-methyl-1,4-dioxa-8-azaspiro[4.5]decan-8-yl)-8-nitro-6-(trifluoromethyl)-4H-1,3-benzothiazin-4-one (10)

(S)-7-Ethyl-2-(2-methyl-1,4-dioxa-8-azaspiro[4.5]decan-8-yl)-8-nitro-6-(trifluoromethyl)-4H-1,3-benzothiazin-4-one (11)

(S)-5-Cyclopropyl-2-(2-methyl-1,4-dioxa-8-azaspiro[4.5]decan-8-yl)-8-nitro-6-(trifluoromethyl)-4H-1,3-benzothiazin-4-one (12)

(S)-5-Ethynyl-2-(2-methyl-1,4-dioxa-8-azaspiro[4.5]decan-8-yl)-8-nitro-6-(trifluoromethyl)-4H-1,3-benzothiazin-4-one (13)

(S)-2-(2-Methyl-1,4-dioxa-8-azaspiro[4.5]decan-8-yl)-8-nitro-4-oxo-6-(trifluoromethyl)-4H-1,3-benzothiazine-7-carbonitrile (14)

(S)-5,7-Dimethyl-2-(2-methyl-1,4-dioxa-8-azaspiro[4.5]decan-8-yl)-8-nitro-6-(trifluoromethyl)-4H-1,3-benzothiazin-4-one (15)

2-(4-(Cyclohexylmethyl)piperazin-1-yl)-5-methyl-8-nitro-6-(trifluoromethyl)-4H-1,3-benzothiazin-4-one (16)

2-(4-(Cyclohexylmethyl)piperazin-1-yl)-7-methyl-8-nitro-6-(trifluoromethyl)-4H-1,3-benzothiazin-4-one (17).

[3] A further preferred embodiment is a compound of formula (I) according to embodiment [2] selected from the group consisting of (S)-5-Methyl-2-(2-methyl-1,4-dioxa-8-azaspiro[4.5]decan-8-yl)-8-nitro-6-(trifluoromethyl)-4H-1,3-benzothiazin-4-one (9b)

2-(4-(Cyclohexylmethyl)piperazin-1-yl)-5-methyl-8-nitro-6-(trifluoromethyl)-4H-1,3-benzothiazin-4-one (16)

The compounds of the invention are useful for the treatment of infectious diseases caused by bacteria. More particularly, the compounds of the invention are useful for the prophylactic and therapeutic treatment of tuberculosis infections and other mycobacterial infections in humans and in animals. Accordingly, a further aspect of the invention is directed to pharmaceutical compositions comprising a compound of formula (I).

[4] Thus, a further aspect of the invention is also concerned with a pharmaceutical composition comprising a compound according to [1] to [3] and/or a pharmaceutically acceptable salt thereof.

Also disclosed is a pharmaceutical composition comprising a compound of formula (I) and/or a pharmaceutically acceptable salt thereof according to embodiment [6] that further comprises one or more pharmaceutically acceptable carriers and/or excipients.

A pharmaceutically acceptable salt of an ionizable version of a compound of the invention is an acid or base salt that is generally considered in the art to be suitable for use in contact with tissues of human beings or animals without excessive toxicity, irritation, allergic response, or other problems or complications. Such salts include mineral and organic acid salts of basic residues such as amines, as well as alkali or organic salts of acidic residues such as carboxylic acids.

Specific pharmaceutically acceptable salts include salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxy benzoic, citric, tartaric, lactic, stearic; salicylic, glutamic, ascorbic, pamoic, succinic, fumaric, maleic, propionic, hydroxymaleic, hydroiodic, phenylacetic, alkanoic such as acetic.

Similarly, pharmaceutically acceptable cations include, but are not limited to sodium, potassium, calcium, aluminum, lithium and ammonium.

Those of ordinary skill in the art will recognize further pharmaceutically acceptable salts for the compounds of the invention, including those listed by Remington's Pharmaceutical Sciences, 17$^{th}$ Ed., Mack Publ. Co., Easton, Pa., p. 1418 (1985).

[5] The invention furthermore relates to a compound for use in a method of treatment of a disease caused by a microbial infection comprising a therapeutically effective amount of a compound of the formula (I) and/or a pharmaceutically acceptable salt thereof or a pharmaceutical composition according to any one of [1] to [4] being administered to a patient in need thereof.

[6] In particular, the compound of formula (I) and/or a pharmaceutically acceptable salt thereof according to the present invention can be used in a method for the treatment of a mycobacterial infection in mammals,

[7] Particularly preferred is the compound of formula (I) and/or a pharmaceutically acceptable salt thereof according to the present invention for use in the therapeutic or prophylactic treatment of tuberculosis or leprosy infection in mammals.

The compounds of the invention can be formulated by use of methods known in the art in the form of a diluted solution or a suspension in pharmaceutically acceptable media for topical or parenteral administration by way of an intravenous, subcutaneous or intramuscular injection or by nasal application. In a preferred method, the new compounds are prepared in the form of a tablet, capsule or aqueous suspension together with pharmaceutically acceptable excipients for oral administration.

Pharmaceutically acceptable excipients are well known in the pharmaceutical art, and are described, for example in Remington's Pharmaceutical Sciences, 17$^{th}$ Ed., Mack Publ. Co., Easton, Pa. (1985). The pharmaceutical excipient can be selected with regard to the intended route of administration and standard pharmaceutical practice.

Furthermore, as demonstrated above, the newly identified reduction pathway is applicable to benzothiazinone compounds. The Meisenheimer complexes with such compounds equally form part of the present invention.

[8] Another aspect of the present invention are isolable, newly identified Meisenheimer complexes of formulae (II)

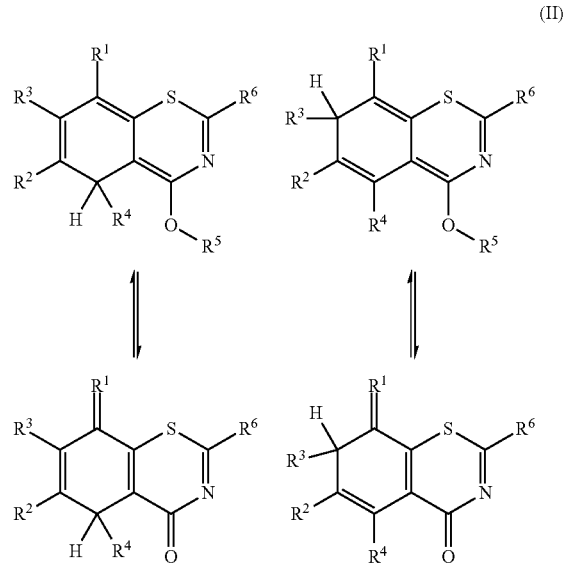

(II)

wherein
$R^1$ and $R^2$ are independently of each other $NO_2$, $NR^7R^8$, $NHOR^9$, —$COOR^9$, CN, $CONR^{10}R^{11}$, CHO, F, Cl, Br, —$SO_2NR^{12}R^{13}$, linear or branched $C_1$-$C_4$ alkoxy, $OCF_3$, mono-, di- or trifluoroalkyl having 1 to 3 carbon atoms; with the proviso that at least one of $R^1$ and $R^2$ are a nitro group; $R^3$, $R^4$ are, independently of each other hydrogen, hydroxyl, —$SR^{14}$, CN, —$N_3$, or a saturated or unsaturated, optionally halogenated, linear or branched aliphatic radical having 1-4 carbon atoms, F, Cl, Br, linear or branched $C_1$-$C_4$ alkoxy;
$R^5$ is hydrogen or an unsaturated or saturated, optionally halogenated linear or branched aliphatic radical having 1 to 6 carbon atoms; acyl containing 1 to 4 carbon atoms, —$CONHR^{10}$ or —$SiR^{12}R^{13}R^{14}$;
$R^6$ is a substituted or unsubstituted heterocycloalkyl, heteroalkyl or heteroaryl substituent;
$R^7$, $R^8$, $R^9$, $R^{10}$, $R^{11}$, $R^{12}$, $R^{13}$, $R^{14}$ are independently of each other selected from hydrogen, an unsaturated or saturated, optionally halogenated, linear or branched aliphatic radical having 1-6 carbon atoms; phenyl; benzyl or acyl having 1-4 carbon atoms.

The different substituents of a compound of formula (II) are defined as follows:

The halogen atom of is a fluorine atom, a chlorine atom, a bromine atom or an iodine atom.

The aliphatic radical is a linear or branched $C_1$-$C_6$ alkyl, $C_2$-$C_6$ alkenyl, $C_2$-$C_6$ alkinyl or a $C_3$-$C_6$ cycloalkyl radical.

The $C_1$-$C_6$ alkyl is a linear or branched alkyl, and includes methyl, ethyl, isopropyl, butyl, isobutyl, secondary butyl, tertiary butyl, pentyl, 3-methylbutyl, neopentyl, hexyl, 2-ethylbutyl.

The $C_1$-$C_4$ alkyl is a linear or branched alkyl, and includes methyl, ethyl, isopropyl, butyl, isobutyl, a secondary or a tertiary butyl.

The $C_2$-$C_6$ alkenyl is a linear or branched alkenyl, and includes vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl.

The $C_2$-$C_6$ alkinyl is a linear or branched alkinyl, and includes ethinyl, propinyl, butinyl, pentinyl, hexinyl.

The $C_3$-$C_6$ cycloalkyl is cyclopropyl, cyclobutyl, cyclopentyl, cyclohexyl.

The aliphatic radical may be substituted by fluorine, chlorine, bromine or iodine.

The $C_1$-$C_4$ alkoxy is a linear or branched alkoxy, and methoxy, ethoxy, propoxy or isopropoxy, butoxy or isobutoxy.

The $C_1$-$C_4$ acyl includes a formyl, acetyl, propionyl and butyryl group.

The heteroaryl is a monocyclic- or polycyclic aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl.

The heteroaryl group can be unsubstituted or substituted with 1-3 substituents selected from $C_1$-$C_6$ alkyl, $C_2$-$C_6$ alkenyl or $C_2$-$C_6$ alkinyl, F, Cl, Br, $C_1$-$C_4$ alkoxy and $C_1$-$C_4$ acyl.

Preferably, a heteroaryl group is a monocyclic ring, wherein the ring comprises 1 to 3 heteroatoms selected from a nitrogen atom, an oxygen atom and a sulfur atom, and 2 to 5 carbon atoms. Particularly preferred is a hetearyl group containing 1 or 2 nitrogen atoms and 0 to 1 atom selected from an oxygen atom and a sulfur atom, and having 5 or 6 ring-constituting atoms and include pyrrolyl, pyrazolyl, imidazolyl, and pyridinyl.

The heterocycloalkyl is a non-aromatic monocyclic or polycyclic ring comprising carbon and hydrogen atoms and at least one heteroatom, preferably, 1 to 4 heteroatoms selected from a nitrogen atom, an oxygen atom, and a sulfur atom. A heterocycloalkyl can have one or more carbon-carbon double bonds or carbon-heteroatom double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetra-hydropyranyl, and pyranyl.

A heterocycloalkyl group can be unsubstituted or substituted with 1-3 substituents selected from $C_1$-$C_6$ alkyl, $C_2$-$C_6$ alkenyl or $C_2$-$C_6$ alkinyl, F, Cl, Br, $C_1$-$C_4$ alkoxy and $C_1$-$C_4$ acyl.

Preferably, the heterocycloalkyl group is a monocyclic or bicyclic ring having one to three heteroatoms. Particularly preferred are the 2-methyl-1,4-dioxa-8-azaspiro[4.5]decan-8-yl and the 4-(cyclohexylmethyl)piperazin-1-yl group.

The heteroalkyl is a linear or branched alkyl comprising carbon and hydrogen atoms and at least one heteroatom, preferably, 1 to 4 heteroatoms selected from a nitrogen atom, and a sulfur atom. A heteroalkyl can have one or more carbon-carbon double bonds or carbon-heteroatom double bonds.

A heteroalkyl group can be unsubstituted or substituted with 1-3 substituents selected from $C_1$-$C_6$ alkyl, $C_2$-$C_6$ alkenyl or $C_2$-$C_6$ alkinyl, F, Cl, Br, $C_1$-$C_4$ alkoxy and $C_1$-$C_4$ acyl.

In a preferred embodiment, the Meisenheimer Complex of the formulae (II) contains heterocycloalkyl, heteroalkyl or heteroaryl groups of $R^6$ that are unsubstituted.

[9] According to another embodiment the heterocycloalkyl, heteroalkyl or heteroaryl group $R^6$ of the Meisenheimer complex of formula (II) according to embodiment [8] is substituted with 1-3 substituents selected from $C_1$-$C_6$ alkyl, $C_2$-$C_6$ alkenyl or $C_2$-$C_6$ alkinyl, F, Cl, Br, $C_1$-$C_4$ alkoxy, $C_1$-$C_4$ acyl.

[10] A further embodiment is an isolable Meisenheimer complex according to the formulae (II), wherein $R^1$ is $NO_2$, $R^2$ is $CF_3$, $R^3$ and $R^4$ each are one or two hydrogens or methyl and hydrogen, $R^5$ is hydrogen or methyl, $R^6$ is 2-methyl-1,4-dioxa-8-azaspiro[4.5]decan-8-yl.

[11] Yet one further embodiment encompasses a Meisenheimer complex according to the formulae (II) of embodiment [8], wherein $R^1$ is $NO_2$, $R^2$ is $CF_3$, $R^3$ and $R^4$ each are one or two hydrogens, $R^5$ is hydrogen or methyl, $R^6$ is a 4-(cyclohexylmethyl)piperazin-1-yl group.

[12] The use of a Meisenheimer complex as claimed in any of the above embodiments [8]-[11] as a research tool to elucidate the metabolism of nitro-substituted benzothiazinone compounds. Thus, the newly identified Meisenheimer complexes of BTZ043 and PBTZ169 also form part of the present invention.

EXPERIMENTAL SECTION

Instrumentation

Analytical HPLC (LC-UV/Vis) was performed on an 1100 Series HPLC system (Agilent Technologies, Inc., Santa Clara, Calif., USA) consisting of MicroALS autosampler, CapPump, ALSTherm, column oven and a DAD. HPLC conditions: Phenomenex column Kinetex 5 μm, XB-C18, 100 Å, 250×4.6 mm and gradient elution (MeCN (0.1% (v/v) TFA): 0.1% (v/v) TFA ($H_2O$); 10:90 to 100:0 in 20 min and 100:0 for further 10 min, flow rate 0.5 mL min$^{-1}$), 3-5 μL injection volume. Buffered LC-MS analyses were carried out on Waters (Waters, Milford, Mass., www.waters.com) ZQ instrument consisting of chromatography module Alliance HT, photodiode array detector 2996, and mass spectrometer Micromass ZQ. HPLC conditions: Waters Pro C18 YMC 3×50 mm column and gradient elution (MeCN: 10 mM ammonium acetate ($H_2O$); 5:95 to 80:20 in 10 min, flow rate 0.7 mL min$^{-1}$). The MS electrospray source operated at capillary voltage 3.5 kV and a desolvation temperature 300° C. LC-HRMS measurements were performed using an Exactive Q Orbitrap high performance benchtop LC-HRMS with an electrospray ion source and an Accela HPLC system (Thermo Fisher Scientific, Bremen, Germany) consisting of an Autosampler equipped with a column oven, a 1250 Pump and a PDA Detector. HPLC conditions: Thermo Scientific column Accucore C18, 2.6 μm, 100×2.1 mm and gradient elution (MeCN (0.1% (v/v) formic acid): 0.1% (v/v) formic acid ($H_2O$); 5:95 to 98:2 in 10 min and 98:2 for further 12 min, flow rate 0.2 mL min-), 3-5 μL injection volume.

Preparative HPLC was performed on a Gilson Abimed equipped with Binary Pump 321 and 156 UV/Vis detector. HPLC conditions: Phenomenex column Luna C18, 10 μm, 250×21.2 mm and gradient elution (MeCN (0.1% (v/v) TFA): 0.1% (v/v) TFA ($H_2O$); flow rate 21 mL min-) for acidic conditions and gradient elution (MeCN: $H_2O$; flow rate 21 mL min-) for neutral conditions. NMR spectra were recorded on Bruker AVANCE III 500 MHz or 600 MHz instrument. Spectra were normalized relative to the residual solvent signals. Following abbreviations were used for multiplicities: s=singlet, d=doublet, t=triplet, q=quartet, qt=quintet.

Chemical Preparations

All chemicals were purchased from commercial suppliers and used without further purification. BTZ043 (1) and PBTZ169 (2) were synthesized in analogy to the known preparation methods as described in detail in WO 2007/134625 A1, WO 2009/010163 A1 and WO 2012/066518 A1.

Reactions were carried out under inert gas (argon) by using the Schlenk technique. Acetonitrile, tetrahydrofuran and diethyl ether were used from an Innovative Technology PureSolv MD-7 EN solvent purification system. Ethyl acetate, acetonitrile and water were degassed by three freeze-pump-thaw-cycles.

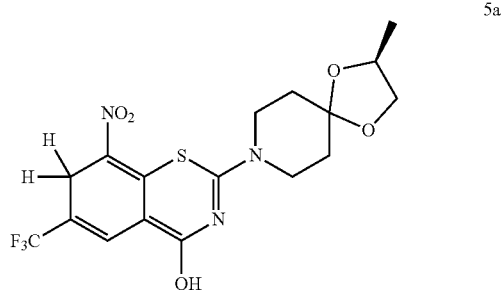

5a

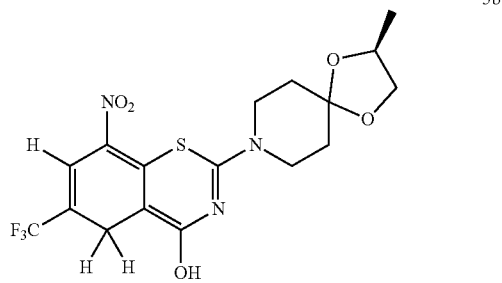

5b

Compound mixture 5a/b: BTZ043 (200 mg, 464 μmol) was dissolved in a mixture of acetonitrile and water (5 mL, 4:1) and sodium borohydride was added slowly until the educt disappeared on TLC analysis. Precipitates formed during the reaction were successively dissolved by the addition of additional water. TFA was slowly added until precipitation of a deep red solid was complete. The mixture was centrifuged and the supernatant was discarded. The residue was washed with water (2×5 mL) and with acetonitrile (2×5 mL) and was dried in fine vacuum to give a crude mixture which mainly contained a/b (175 mg, 5a:5b≈7:3, approx. 404 μmol, approx. 87%). This material was used without further purification for subsequent chemical derivatization.

$^1$H NMR (500 MHz; THF-D8): δ=1.25 (d, 3H, $^3J_{HH}$=6.1 Hz, (CH$_3$)—CH), 1.77-1.88 (m, 4H, CH$_2$—C(O)$_2$—CH$_2$), 3.46 (t, 1H, $^3J_{HH}$=7.8 Hz, O—CH$_2$), 3.56 (m, 0.6 H, CH$_2$—C—CF$_3$), 3.73 (m, 1.4 H, CH$_2$—C—NO$_2$), 3.88-4.04 (m, 4H, (CH$_2$)$_2$—N), 4.09 (dd, 1H, $^2J_{HH}$=5.7 Hz, $^3J_{HH}$=7.9 Hz, O—CH'$_2$), 4.26 (m, 1H, CH$_3$—CH), 7.08 (st, 0.7 H, $^3J_{HH}$=1.5 Hz, CH—C—NO$_2$), 7.32 (m, 0.3 H, CH—C—CF$_3$) ppm. MS (LC-ESI$^+$) 5a: m/z (%)=434 [M+H]$^+$ (100), 867 [2M+H]$^+$ (5); 5b: m/z (%)=432 [M+H]$^+$ (100), 867 [2M+H]$^+$ (5). HRMS (ESI$^+$) calcd. for C$_{17}$H$_{19}$F$_3$O$_5$N$_3$S$^+$: 434.0992; found: 5a: 434.0988, 5b: 434.0988.

Compound 5b: In a parallel experiment analytical samples of 5b (reference material) were generated by preparative HPLC of the crude reaction product of 5a/b (prior to TFA precipitation) under acidic conditions (15-70% acetonitrile in 40 min). The material was relatively stable when all solvents were immediately removed and the dry product was stored under inert gas. Rapid oxidation occurred in solution, in particular in the presence of atmospheric oxygen. Complete recovery of the desired compound was found critical even under proper inert handling conditions.

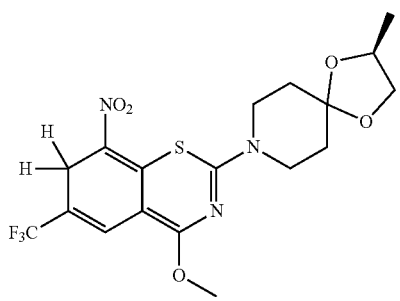

6a

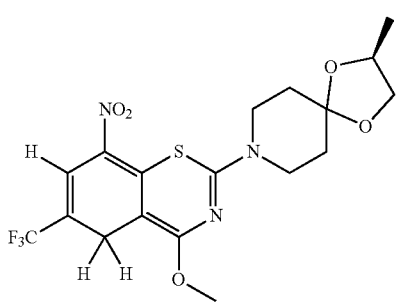

6b

Compounds 6a/b: The compound mixture of 5a/b (175 mg, approx. 404 μmol) was taken up in acetonitrile (8 mL), dimethyl sulfate (140 μL, 186 mg, 1.48 mmol) and triethyl amine (200 μL, 146 mg, 1.44 mmol) were slowly added, and the mixture was stirred at room temperature for 70 min and additional 60 min subsequent to the addition of methanol (200 μL, 158 mg, 4.93 mmol). The red solution was diluted with ethyl acetate (30 mL) and washed with hydrochloric acid (2×50 mL, 2 M). The organic layer was dried with sodium sulfate and evaporated to dryness. The residue was taken up in acetonitrile, centrifuged, and the supernatant was subjected to preparative HPLC (neutral conditions, 40-70% acetonitrile in 60 min) to give pure 6a (retention time=28 min, 17 mg, 8%) and 6b (retention time=47 min, 4 mg, 2%).

Compound 6a: $^1$H NMR (500 MHz; CD$_3$CN): δ=1.25 (d, 3H, $^3J_{HH}$=6.1 Hz,(CH$_3$)—CH), 1.77-1.92 (m, 4H, CH$_2$—C(O)$_2$—CH$_2$), 3.48 (t, 1H, $^3J_{HH}$=7.8 Hz, O—CH$_2$), 3.66 (qt, 2H, $^3J_{HH}$=1.6 Hz, CH$_2$—C—NO$_2$), 3.77-4.16 (m, 4H, (CH$_2$)$_2$—N), 3.92 (s, 3H,CH$_3$—O), 4.10 (dd, 1H, $^2J_{HH}$=5.8 Hz, $^3J_{HH}$=8.1 Hz, O—CH'$_2$), 4.28 (m, 1H, CH$_3$—CH), 6.99 (st, 1H, $^3J_{HH}$=1.6 Hz, CH—C—CF$_3$) ppm. $^{13}$C NMR (125.8 MHz; CD$_3$CN): δ=18.8 (1C, CH$_3$—C), 28.3 (1C, CH$_2$—C—NO$_2$), 35.5 (1C, CH$_2$—C(O)$_2$), 36.7 (1C, C'H$_2$—C(O)$_2$), 45.8 (1C, CH$_2$—N—CH$_2$), 55.8 (1C, CH$_3$—O), 71.5 (1C, CH$_2$—O), 73.4 (1C, CH—CH$_3$), 92.6 (1C, C=C—O), 107.3 (1C, C(O)$_2$), 119.7 (1C, $^2J_{CF}$=31.5 Hz, C—CF$_3$), 122.7 (1C, $^3J_{CF}$=6.3 Hz, CH—C—CF$_3$), 122.8 (1C, C—C—NO$_2$), 125.2 (1C, J$_{CF}$=269.8 Hz, CF$_3$), 146.3 (1C, C—NO$_2$), 165.2 (1C, S—C=N), 166.1 (1C, C=C—O) ppm. MS (LC-ESI$^+$): m/z (%)=448 [M+H]$^+$ (100), 895 [2M+H]$^+$ (5). HRMS (ESI$^+$) calcd. forC$_{18}$H$_{21}$F$_3$O$_5$N$_3$S$^+$: 448.1149; found: 448.1149.

Compound 6b: $^1$H NMR (500 MHz; CD$_3$CN): δ=1.25 (d, 3H, $^3J_{HH}$=6.1 Hz, (CH$_3$)—CH), 1.77-1.92 (m, 4H, CH$_2$—C(O)$_2$—CH$_2$), 3.48 (t, 1H, J$_{HH}$=7.9 Hz, O—CH$_2$), 3.52 (qt, 2H, $^3J_{HH}$=1.7 Hz, CH$_2$—C—CF$_3$), 3.77-4.20 (m, 4H, (CH$_2$)$_2$—N), 3.99 (s, 3H, CH$_3$—O), 4.10 (dd, 1H, $^2J_{HH}$=5.8 Hz, $^3J_{HH}$=8.0 Hz, O—CH'$_2$), 4.28 (m, 1H, CH$_3$—CH), 7.29 (st, 1H, $^3J_{HH}$=1.6 Hz, CH—C—NO$_2$) ppm. $^{13}$C NMR (125.8 MHz; CD$_3$CN): δ=18.8 (1C, CH$_3$—C), 25.4 (1C, CH$_2$—C—CF$_3$), 35.4 (1C, CH$_2$—C(O)$_2$), 36.6 (1C, C'H$_2$—C(O)$_2$), 45.8 (1C, CH$_2$—N—CH$_2$), 56.5 (1C, CH$_3$—O), 71.6 (1C, CH$_2$—O), 73.4 (1C, CH—CH$_3$), 98.4 (1C, C=C—O), 107.2 (1C, C(O)$_2$), 114.9 (1C, $^2J_{CF}$=31.5 Hz, C—CF$_3$), 121.1 (1C, C—C—NO$_2$), 124.2 (1C, $^3J_{CF}$=6.4 Hz, CH—C—CF$_3$), 125.3 (1C, J$_{CF}$=269.8 Hz, CF$_3$), 149.0 (1C, C—NO$_2$), 167.1 (1C, S—C=N), 169.5 (1C, C=C—O) ppm. MS (LC-ESI$^+$): m/z (%)=448 [M+H]$^+$ (100), 895 [2M+H]$^+$ (5). HRMS (ESI$^+$) calcd. for C$_{18}$H$_{21}$F$_3$O$_5$N$_3$S$^+$: 448.1149; found: 448.1142.

The new Example compounds 9a/b of formula (I) have been synthesized according to methods that are generally analogous to the method described above.

General Procedure:

The unsubstituted benzothiazinone (0.46 mmol; BTZ043 or PBTZ169) was dissolved in anhyd. THF (5-10 ml), cooled to −78° C. and a solution of the corresponding metal-organic reagent (1.6-2.2 eq) was added dropwise. When using an organolithium compound, a solution of the benzothiazinone in THF was added to the preformed organometal species. After complete addition the mixture was stirred for 1-18 h. DDQ (1.7-2.3 eq) was added and the mixture was stirred for 3 h at 0° C. The reaction mixture was diluted with ethyl acetate (100 mL), washed with sat. NaHCO$_3$ (4×75 ml), water (75 ml) and brine (75 ml). The organic solution was dried with Na$_2$SO$_4$ and concentrated under reduced pressure. Purification of the residue was conducted by column chromatography (SiO$_2$, light petroleum—EtOAc or light petroleum—DCM—acetone).

Example 9a and Example 9b

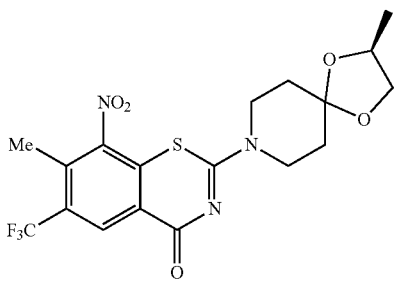

9a

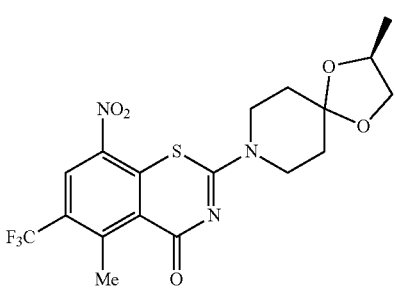

9b

Compounds 9a/b. To a solution of 1 (146 mg, 0.34 mmol) in diethyl ether (3 mL) and tetrahydrofuran (3 mL) was slowly added MeMgBr (340 µL, 0.34 mmol, 1 M, in dibutyl ether). The solution was stirred for two hours at room temperature, water (5 mL) was added and the mixture was extracted with ethyl acetate (2×35 mL), dried with sodium sulfate and concentrated under reduced pressure. The residue was taken up in methanol and purified by preparative HPLC (10%-100% acetonitrile in 10 min) to afford 9a (20 mg, 13%) and 9b (5 mg, 3%).

Alternatively, following the general procedure with MeMgBr (0.3 M in THF) 40 mg (19%, 0.09 mmol) of 9b and 27 mg (13%, 0.06 mmol) of 9a were obtained as a light yellow solid.

Compound Example 9a ((S)-7-Methyl-2-(2-methyl-1,4-dioxa-8-azaspiro[4.5]decan-8-yl)-8-nitro-6-(trifluoromethyl)-4H-1,3-benzothiazin-4-one)

$^1$H-NMR (300 MHz, CDCl$_3$): δ=1.27 (d, J=6.2 Hz, 3H, (CH$_3$)—CH), 1.78-1.83 (m, 4H, CH$_2$—C(O)$_2$—CH$_2$), 2.48 (d, J=1.0 Hz, 3H, CH$_3$—C), 3.46 (t, J=7.8 Hz, 1H, O—CH$_2$), 3.79 (bs, 2H, (CH$_2$)$_2$—N), 4.07 (dd, J=8.0, 5.9 Hz, 1H, O—CH'$_2$), 4.11-4.30 (m, 3H, (CH$_2$)$_2$—N, CH$_3$—CH), 8.81 (s, 1H, CH—C—CF$_3$).

$^{13}$C-NMR (75 MHz, CDCl$_3$): δ=14.7 (q, J=2.6 Hz), 18.2, 35.1, 36.2, 44.6 (br), 70.8, 72.4, 106.2, 122.2, 122.6 (q, J=274.8 Hz), 129.51 (q, J=32.1 Hz), 129.53 (q, J=6.1 Hz), 134.0, 148.5, 159.3, 166.6.

m/z [M+H]$^+$ calcd for C$_{18}$H$_{19}$F$_3$N$_3$O$_5$S: 446.0992; found: 446.0995.

Example 9b ((S)-5-Methyl-2-(2-methyl-1,4-dioxa-8-azaspiro[4.5]decan-8-yl)-8-nitro-6-(trifluoromethyl)-4H-1,3-benzothiazin-4-one)

$^1$H-NMR (300 MHz, CDCl$_3$): δ=1.28 (d, J=6.2 Hz, 3H, (CH$_3$)—CH), 1.77-1.84 (m, 4H, CH$_2$—C(O)$_2$—CH$_2$), 2.83 (s, 3H, CH$_3$—C), 3.47 (t, J=7.8 Hz, 1H, O—CH$_2$), 3.74-4.05 (bs, 4H, (CH$_2$)$_2$—N), 4.09 (dd, J=8, 5.7 Hz, 1H, O—CH'$_2$), 4.21-4.31 (m, 1H, CH$_3$—CH), 8.64 (s, 1H, CH—C—CF$_3$).

$^{13}$C-NMR (75 MHz, CDCl$_3$): δ=18.3 (q, J=2.2 Hz), 35.1 (br), 36.2 (br), 44.5 (br), 70.8, 72.4, 106.3, 117.3, 121.0, 122.8 (q, J=274.2 Hz), 124.6 (q, J=6.6 Hz), 129.4 (q, J=31 Hz), 133.5, 141.7, 147.0, 160.1, 169.7.

HRMS (ESI): m/z [M+H]$^+$ calcd for C$_{18}$H$_{19}$F$_3$N$_3$O$_5$S: 446.0992; found: 446.0996.

Example 10 ((S)-5-Ethyl-2-(2-methyl-1,4-dioxa-8-azaspiro[4.5]decan-8-yl)-8-nitro-6-(trifluoromethyl)-4H-1,3-benzothiazin-4-one)

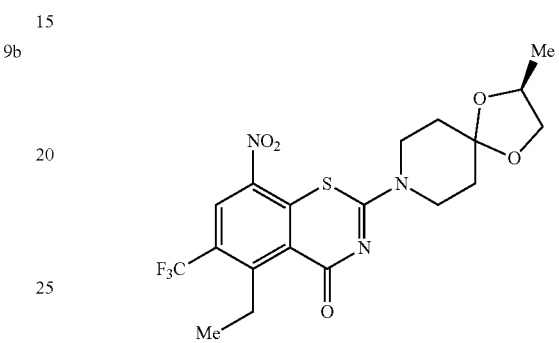

Following the general procedure with BTZ043 and EtMgBr (0.3 M in THF) 31 mg (15%, 0.07 mmol) of the title compound were obtained as a light yellow solid.

$^1$H-NMR (300 MHz, CDCl$_3$): δ=1.25 (d, $^3$J$_{HH}$=7.7 Hz, 3H, CH$_3$—CH$_2$), 1.29 (d, J=5.9 Hz, 3H, (CH$_3$)—CH), 1.73-1.90 (m, 4H, CH$_2$—C(O)$_2$—CH$_2$), 3.41-3.51 (m, 3H, CH$_2$—C, O—CH'$_2$), 3.95 (bs, 4H, (CH$_2$)$_2$—N), 4.09 (dd, J=8.0, 5.7 Hz, 1H, O—CH'$_2$), 4.22-4.32 (m, 1H, CH$_3$—CH), 8.65 (s, 1H, CH—C—CF$_3$).

$^{13}$C-NMR (75 MHz, CDCl$_3$): δ=16.2, 18.3, 23.2 (d, J=1.7 Hz), 35.1 (br), 36.3 (br), 44.7 (br), 70.8, 72.4, 106.4, 122.9 (q, J=274.8 Hz), 124.9 (q, J=6.1 Hz), 128.8 (q, J=31.5 Hz), 129.9, 133.8, 142.2, 153.0, 159.9, 170.1.

HRMS (ESI): m/z [M+H]$^+$ calcd for C$_{19}$H$_{21}$F$_3$N$_3$O$_5$S: 460.1149; found: 460.1151.

Example 11 ((S)-7-Ethyl-2-(2-methyl-1,4-dioxa-8-azaspiro[4.5]decan-8-yl)-8-nitro-6-(trifluoromethyl)-4H-1,3-benzothiazin-4-one)

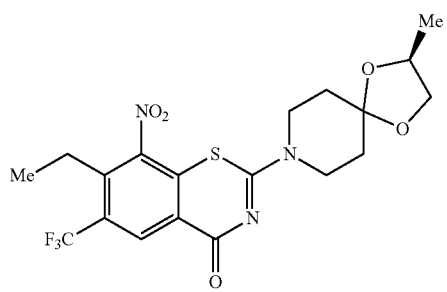 [SMILES: CCc1c(C(F)(F)F)cc2c(=O)nc(N3CCC4(CC3)OC[C@H](C)O4)sc2c1[N+](=O)[O-]]

Following the general procedure with BTZ043 and EtMgBr (0.3 M in THF) 32 mg (15%, 0.07 mmol) of the title compound were obtained as an off white solid.

$^1$H-NMR (300 MHz, CDCl$_3$): δ=1.25 (d, J=7.2 Hz, 3H, CH$_3$—CH$_2$), 1.29 (d, J=6.2 Hz, 3H, (CH$_3$)—CH), 1.75-1.88

(m, 4H, CH$_2$—C(O)$_2$—CH$_2$), 2.88 (q, J=7.4 Hz, 2H, CH$_3$—CH$_2$), 3.48 (t, J=7.8 Hz, 1H, O—CH$_2$), 3.70-4.32 (m, 6H, (CH$_2$)$_2$—N, O—CH'$_2$, CH$_3$—CH), 8.86 (s, 1H, CH═C—CF$_3$).

$^{13}$C-NMR (75 MHz, CDCl$_3$): δ=15.2 (d, J=1.1 Hz), 18.3, 22.2 (d, J=2.2 Hz), 35.1 (br), 36.3 (br), 44.7 (br), 70.9, 72.5, 106.3, 117.6, 122.3, 123.8 (q, J=274.2 Hz), 129.4 (q, J=32.1 Hz), 130.0 (q, J=5.7 Hz), 139.4, 148.8, 159.3, 166.7.

m/z [M+H]$^+$ calcd for C$_9$H21F$_3$N$_3$O$_5$S: 460.1149; found: 460.1151.

Example 12 ((S)-5-Cyclopropyl-2-(2-methyl-1,4-dioxa-8-azaspiro[4.5]decan-8-yl)-8-nitro-6-(trifluoromethyl)-4H-1,3-benzothiazin-4-one)

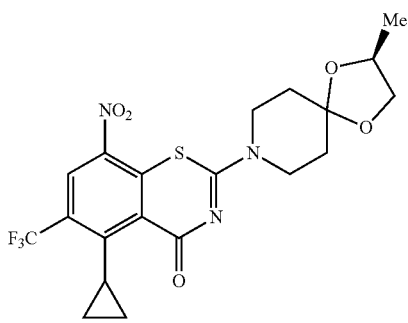 [SMILES: C[C@H]1COC2(CCN(c3nc(=O)c4c(C5CC5)c(C(F)(F)F)cc([N+](=O)[O-])c4s3)CC2)O1]

Following the general procedure with BTZ043 and cyclopropylmagnesium bromide (0.5 M in THF) 42 mg (19%, 0.09 mmol) of the title compound were obtained as a light yellow solid.

$^1$H-NMR (300 MHz, CDCl$_3$): δ=0.57 (q, J=5.9 Hz, 2H, CH$_2$—CH$_2$), 1.18-1.25 (m, 2H, CH'$_2$—CH'$_2$), 1.29 (d, J=5.9 Hz, 3H, (CH$_3$)—CH), 1.75-1.88 (m, 4H, CH$_2$—C(O)$_2$—CH$_2$), 2.47-2.57 (m, 1H, CH$_2$—CH—CH$_2$), 3.48 (t, J=8.0 Hz, 1H, O—CH$_2$), 3.96 (bs, 4H, (CH$_2$)$_2$—N), 4.09 (dd, J=8.0, 5.7 Hz, 1H, O—CH'$_2$), 4.22-4.32 (m, 1H, (CH$_3$)—CH), 8.61 (s, 1H, CH═C—CF$_3$).

$^{13}$C-NMR (75 MHz, CDCl$_3$): δ=9.4, 14.7, 18.3, 35.1 (br), 36.3 (br), 44.7 (br), 70.8, 72.4, 106.3, 122.3 (q, J=275.3 Hz), 124.8 (q, J=6.1 Hz), 131.8 (q, J=32.6 Hz), 132.5, 132.9, 141.4, 151.4, 159.9, 170.0.

HRMS (ESI): m/z [M+H]$^+$ calcd for C$_{20}$H2F$_3$N$_3$O$_5$S: 472.1149; found: 472.1153.

Example 13 ((S)-5-Ethynyl-2-(2-methyl-1,4-dioxa-8-azaspiro[4.5]decan-8-yl)-8-nitro-6-(trifluoromethyl)-4H-1,3-benzothiazin-4-one)

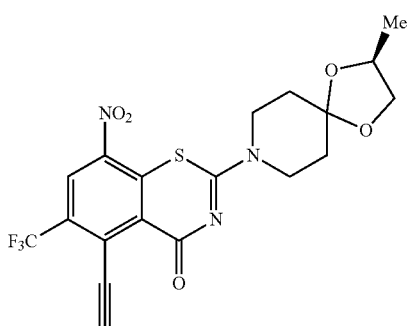 [SMILES: C#Cc1c(C(F)(F)F)cc([N+](=O)[O-])c2sc(N3CCC4(CC3)OC[C@H](C)O4)nc(=O)c12]

Following the general procedure with [2-(trimethylsilyl)ethynyl]-lithium and BTZ043 45 mg (19%, 0.09 mmol) of a light brown oil was obtained of which 25 mg (0.05 mmol) was dissolved in THF (1 mL) and MeOH (1 mL), KF (8.3 mg, 0.14 mmol) was added and the mixture was stirred at ambient temperature for 1.5 h. The mixture was diluted with ethyl acetate (15 mL), washed with half saturated NaHCO$_3$ (2×10 mL), brine (10 mL) and dried with Na$_2$SO$_4$. After concentration under reduced pressure the residue was purified by column chromatography (SiO$_2$, light petroleum—DCM—acetone, 4:4:1) to give 20 mg (93%, 0.044 mmol) of a light sensitive grey solid.

$^1$H-NMR (300 MHz, CDCl$_3$): δ=1.30 (d, J=5.9 Hz, 3H, (CH$_3$)—CH), 1.76-1.89 (m, 4H, CH$_2$—C(O)$_2$—CH$_2$), 3.49 (t, J=7.8 Hz, 1H, O—CH$_2$), 3.80-4.33 (m, 7H, (CH$_2$)$_2$—N, O—CH'$_2$, —CH, (CH$_3$)—CH), 8.70 (s, 1H, CH═C—CF$_3$).

$^{13}$C-NMR (75 MHz, CDCl$_3$): δ=18.3, 35.2 (br), 36.3 (br), 44.9 (br), 70.9, 72.5, 76.2, 96.6, 106.3, 121.9 (q, J=274.8 Hz), 124.8 (q, J=5.5 Hz), 127.4, 132.5, 133.2 (q, J=32.6 Hz), 134.1, 142.2, 159.8, 167.3.

HRMS (ESI): m/z [M+H]$^+$ calcd for C$_{19}$H$_{17}$F$_3$N$_3$O$_5$S: 456.0836; found: 456.0832.

Example 14 ((S)-2-(2-Methyl-1,4-dioxa-8-azaspiro[4.5]decan-8-yl)-8-nitro-4-oxo-6-(trifluoromethyl)-4H-1,3-benzothiazine-7-carbonitrile)

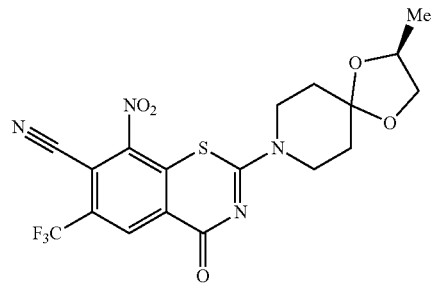 [SMILES: C[C@H]1COC2(CCN(c3nc(=O)c4cc(C(F)(F)F)c(C#N)c([N+](=O)[O-])c4s3)CC2)O1]

A solution of BTZ043 (200 mg, 0.46 mmol) in anhydrous THF (7 mL) was cooled to −78° C. and a solution of n-Bu$_4$NCN (157 mg, 0.56 mmol) in anhydrous THF (3 mL) was added dropwise. After complete addition the mixture was stirred for 1 h at −78° C. and then DDQ (175 mg, 0.77 mmol) was added. The mixture was warmed to 0° C. and stirred for 18 h. After dilution with ethyl acetate (100 mL) the mixture was washed with sat. NaHCO$_3$ (4×50 mL), brine (50 mL) and dried with Na$_2$SO$_4$. After concentration under reduced pressure the residue was purified by column chromatography (SiO$_2$, light petroleum—DCM—acetone, 5:5:1 and CHCl$_3$—MeOH, 50/1) and recrystallization from MeCN, to give 50 mg (24%, 0.11 mmol) of the title compound as a yellow solid.

$^1$H-NMR (500 MHz, DSMO-d$_6$): δ=1.22 (d, J=6.0 Hz, 3H, (CH$_3$)—CH), 1.80 (bs, 4H, CH$_2$—C(O)$_2$—CH$_2$), 3.45 (t, J=7.7 Hz, 1H, O—CH$_2$), 3.88 (bs, 2H, (CH$_2$)$_2$—N), 3.98 (bs, 2H, (CH$_2$)$_2$—N), 4.10 (dd, J=8.0, 5.8 Hz, 1H, O—CH'$_2$), 4.22-4.28 (m, 1H, (CH$_3$)—CH), 8.81 (s, 1H, CH═C—CF$_3$).

$^{13}$C-NMR (125 MHz, DSMO-d$_6$): δ=18.3, 34.4 (br), 35.7 (br), 44.3 (br), 44.8 (br), 70.0, 71.8, 106.0, 109.3, 111.1, 121.5 (q, J=274.3 Hz), 128.3, 130.2 (q, J=33.3 Hz), 130.3 (q, J=4.9 Hz), 134.9, 147.8, 160.5, 164.6.

HRMS (ESI): m/z $[M+H]^+$ calcd for $C_8H_{16}F_3N_4O_5S$: 457.0788; found: 457.0788.

Example 15 ((S)-5,7-Dimethyl-2-(2-methyl-1,4-dioxa-8-azaspiro[4.5]decan-8-yl)-8-nitro-6-(trifluoromethyl)-4H-1,3-benzothiazin-4-one)

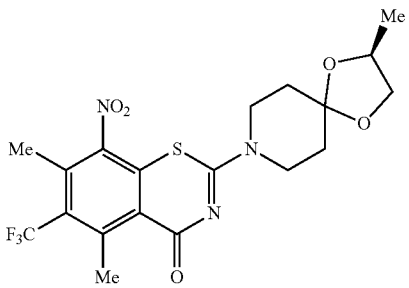 [SMILES: Cc1c(C(F)(F)F)c(C)c2c(=O)nc(N3CCC4(CC3)OC[C@H](C)O4)sc2c1[N+](=O)[O-]]

Following the general procedure using 9a (207 mg, 0.46 mmol) and MeMgBr (3 M in THF) 25 mg (11.7%, 0.05 mmol) of the title compound were obtained as an off white solid.

$^1$H-NMR (300 MHz, $CDCl_3$): δ=1.29 (d, J=5.9 Hz, 3H, $(CH_3)$—CH), 1.75-1.82 (m, 4H, $CH_2$—$C(O)_2$—$CH_2$), 2.46 (q, J=3.3 Hz, 3H, —$CH_3$), 2.80 (q, J=3.3 Hz, 3H, —$CH_3$), 3.47 (t, J=7.8 Hz, 1H, O—CH'$_2$), 3.82 (bs, 2H, $(CH_2)_2$—N), 4.00 (bs, 2H, $(CH_2)_2$—N), 4.09 (dd, J=8.0, 5.7 Hz, 1H, $(CH_3)$—CH), 4.21-4.32 (m, 1H, CH—C—$CF_3$).

$^{13}$C-NMR (75 MHz, $CDCl_3$): δ=16.1 (q, J=5.2 Hz), 18.3, 19.3 (q, J=5.0 Hz), 35.1 (br), 36.3 (br), 70.8, 72.4, 106.4, 124.3 (q, J=277.5 Hz), 126.8, 128.2, 129.9 (q, J=29.3 Hz), 132.2 (d, J=1.1 Hz), 143.6, 147.6, 157.7, 169.6.

HRMS (ESI): m/z $[M+H]^+$ calcd for $C_{19}H_{21}F_3N_3O_5S$: 460.1149; found: 460.1143.

Example 16 (2-(4-(Cyclohexylmethyl)piperazin-1-yl)-5-methyl-8-nitro-6-(trifluoromethyl)-4H-1,3-benzothiazin-4-one)

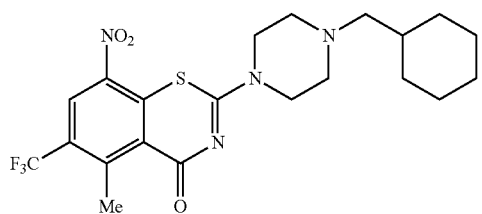 [SMILES: Cc1c(C(F)(F)F)cc([N+](=O)[O-])c2sc(N3CCN(CC4CCCCC4)CC3)nc(=O)c12]

Following the general procedure by using PBTZ169 (CAS [1377239-83-2]) and MeMgCl (3 M in THF) 53 mg (24%, 0.11 mmol) of the title compound were obtained as an orange solid.

$^1$H-NMR (300 MHz, $CDCl_3$): δ=0.80-0.93 (m, 2H, $CH_2$—$CH_2$), 1.09-1.31 (m, 3H, $CH_2$—$CH_2$), 1.40-1.55 (m, 1H, CH'$_2$), 1.64-1.78 (m, 5H, 2×$CH_2$, CH'$_2$), 2.16 (d, J=7.2 Hz, 2H, $CH_2$), 2.49 (t, J=4.9 Hz, 4H, $(CH_2)_2$—N), 2.86 (d, J=1.3 Hz, 3H, $CH_3$—C), 3.90 (bs, 4H, $(CH_2)_2$—N), 8.66 (s, 1H, CH—C—$CF_3$).

$^{13}$C-NMR (75 MHz, $CDCl_3$): δ=18.3, 26.0, 26.7, 31.7, 35.0, 46.9 (br), 53.0 (br), 65.1, 122.8 (q, J=274.8 Hz), 124.7 (q, J=6.1 Hz), 129.6 (q, J=31.5 Hz), 130.2, 133.5, 141.7, 147.1, 160.4, 169.7. HRMS (ESI): m/z $[M+H]^+$ calcd for $C_{21}H_{26}F_3N_4O_3S$: 471.1672; found: 471.1678.

Example 17 (2-(4-(Cyclohexylmethyl)piperazin-1-yl)-7-methyl-8-nitro-6-(trifluoromethyl)-4H-1,3-benzothiazin-4-one)

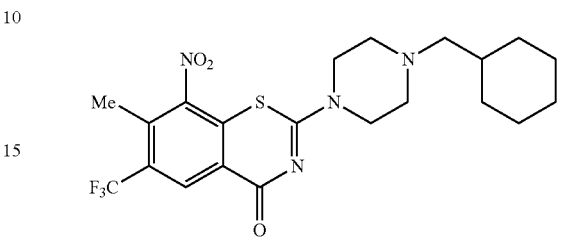

Following the general procedure by using PBTZ169 (CAS [1377239-83-2]) and MeMgCl (3 M in THF) 85 mg (39%, 0.18 mmol) of the title compound were obtained as an orange solid.

$^1$H-NMR (300 MHz, $CDCl_3$): δ=0.79-0.92 (m, 2H, $CH_2$—$CH_2$), 1.09-1.31 (m, 3H, $CH_2$—$CH_2$), 1.41-1.58 (m, 1H, CH'$_2$), 1.63-1.81 (m, 5H, 2×$CH_2$, CH'$_2$), 2.16 (d, J=7.2 Hz, 2H, $CH_2$), 2.47-2.53 (m, 7H, $CH_3$—C, 2×$CH_2$), 3.72 (bs, 2H, CH2-N), 4.10 (bs, 2H, $CH_2$—N), 8.85 (s, 1H, CH—C—$CF_3$).

$^{13}$C-NMR (75 MHz, $CDCl_3$): δ=14.8, 26.0, 26.7, 31.6, 34.9, 46.7 (br), 52.9 (br), 65.0, 122.4, 122.7 (q, J=274.2 Hz), 129.5 (q, J=32.1 Hz), 129.7 (q, J=5.5 Hz), 129.73, 134.0, 148.5, 159.7, 166.6.

HRMS (ESI): m/z $[M+H]^+$ calcd for $C_{21}H_{26}F_3N_4O_3S$: 471.1672; found: 471.1678.

Bioanalytical Procedures

All animal experiments were performed at ATRC (Aurigon Toxicological Research Centre, Dunakeszi, Hungary).

Minipig plasma samples: Minipigs received oral doses of 360 mg/kg BTZ043. Blood was collected 2 h subsequent to administration of the compound formulation, immediately cooled on ice and centrifuged at 4° C. and 3000 rpm to yield plasma aliquots which were snap frozen and stored at −80° C. Plasma aliquots (50 µL) were mixed with acetonitrile (200 µL) on ice and under inert conditions (Don Whitley Scientific, anaerobic workstation), vortexed, treated in an ultrasonic bath (3-5 s) and centrifuged at 4° C. and 9750 rpm. The supernatants were concentrated with a nitrogen stream to a residual volume of approximately 40 µL and analyzed by HPLC and LC-HRMS.

Rat plasma samples: Female Wistar received oral doses of 170 mg/kg BTZ043. Blood was collected ($K_3$-EDTA) 2 h subsequent to administration of the compound formulation under isoflurane anesthesia, immediately cooled on ice and centrifuged at 4° C. and 3000 rpm to yield plasma aliquots which were snap frozen and stored at −80° C. Plasma aliquots (50 µL) were mixed with acetonitrile (200 µL) on ice and under inert conditions (Don Whitley Scientific, anaerobic workstation), vortexed, treated in an ultrasonic bath (3-5 s) and centrifuged at 4° C. and 9750 rpm. The supernatants were concentrated with a nitrogen stream to a residual volume of approximately 40 µL and analyzed by HPLC and LC-HRMS.

Fresh Blood Assay

Human: A BTZ043 solution in DMSO (5 mg/mL) was prepared and 1 µL of this solution was added to 1 mL aliquots fresh whole blood. The mixtures were shaken at 37° C. for 2 h or 16 h and centrifuged at 4° C. and 3000 rpm to yield plasma. Plasma samples (60 µL) were mixed with acetonitrile (240 µL) on ice, vortexed, treated in an ultrasonic bath (3-5 s) and centrifuged at 4° C. and 9750 rpm. The supernatants were concentrated with a nitrogen stream to a residual volume of approximately 40 µL and analyzed by HPLC and LC-HRMS.

Mice: Fresh whole blood was collected from C57BL/6J mice after cervical dislocation under isoflurane anesthesia. Test item solutions were prepared in DMSO (5 mg/mL) and 0.4 µL of this solution was added to 400 µL fresh whole blood. The mixtures were incubated at 37° C. for 4 h and centrifuged at 4° C. and 3000 rpm to yield plasma. Plasma samples (50 µL) were mixed with acetonitrile (200 µL) on ice, vortexed, treated in an ultrasonic bath (3-5 s) and centrifuged at 4° C. and 9750 rpm. The supernatants were concentrated with a nitrogen stream to a residual volume of approximately 40 µL and analyzed by HPLC and LC-HRMS.

Yeast assay: Fresh commercial baker's yeast (200 mg wet mass) was suspended in potassium phosphate buffer (pH 7.5, 100 mM) under anaerobic conditions (Don Whitley Scientific, anaerobic workstation) and a solution of BTZ043 in DMSO (5 µL, 5 mg/mL) was added. The mixture was incubated at 37° C. for 5 min, mixed with acetonitrile (200 µL) on ice and centrifuged at 4° C. and 9750 rpm. The supernatants were concentrated with a nitrogen stream to a residual volume of approximately 40 µL and analyzed by HPLC. See FIG. 4.

Relative Hydride Meisenheimer Complex (HMC) Formation

Fresh whole blood was collected from C57BL/6J mice after euthanasia. Test item solutions were prepared in DMSO (typically 10 mg/mL, less soluble compounds lower) and 0.5 µL of each solution was added to 300 µL aliquots of fresh whole blood under inert conditions (Glovebox, <20 ppm $O_2$). The mixtures were incubated at 37° C. for 4 h (750 rpm) and centrifuged at 4° C. and 3000 rpm to yield plasma. Plasma aliquots (25 µL) were stored at −45° C. and thawed not earlier than 1.5 h prior to LC-HRMS measurement. Aliquots were immediately mixed with acetonitrile (75 µL, containing 2.5 µg·mL$^{-1}$ [$D_4$]-BTZ043 as internal standard) on ice, vortexed, and centrifuged at 4° C. and 16.1 krcf. The supernatants were transferred to air sealed vials and analyzed by LC-HRMS. All samples were prepared in duplicates. Hydride Meisenheimer complex (HMC) formation was calculated as the quotient of the area of the [M+2H+H]$^+$ peak(s) and the sum of the [M+H]$^+$ and the [M+2H+H]$^+$ peak areas in the respective extracted ion chromatograms of each test item (5 ppm window). Relative HMC formation was calculated as the quotient of HMC formation of each derivative and the HMC formation of BTZ043 in the same assay.

Resazurin Microtiter Assay (REMA)

The assay was carried out as previously described (Palomino et al.; Resazurin microtiter assay plate: simple and inexpensive method for detection of drug resistance in *Mycobacterium tuberculosis*. Anticrob. Agents. Chemother. 46(8), 2720-2 (2002). 100 µl of bacterial suspension were used as inoculum per well. 100 µl of serial two-fold dilutions of substance working solution were given in each deepening of a sterile, polystyrene 96-well flat-bottom plate (BD). A drug free growth control and a MTB free sterility control of the medium were included in each plate. Two hundred microliters of sterile water were added to all outer perimeter wells to avoid evaporation during incubation. Plates were then covered with self-adhesive membranes and incubated at 37° C. After 7 days, the assay was stained by adding 30 µl of a freshly prepared solution of 0.02% Resazurin (Sigma-Aldrich, Germany). The plates were re-incubated for additional 24 h at 37° C. A change in color from blue (oxidized state) to pink (reduced state) indicated growth of the bacteria, and the MIC was defined as the lowest concentration of drug that prevented this change in color. Each lot of REMA plates was quality assured by evaluating the range of MIC (4 µg/mL-63 pg/mL).

Cytotoxicity Determination

The test items were dissolved in DMSO (typically 10 mg/mL, less soluble compounds lower). The solutions were diluted in RPMI 1640 medium. HeLa cells (DSM ACC 57) were grown in RPMI 1640 and harvested at the logarithmic growth phase after soft trypsinization using 0.25% trypsin in phosphate buffered saline (PBS) containing 0.02% ethylenediaminetetraacetic acid (EDTA). For each experiment, approximately 10,000 cells were seeded with 0.1 mL culture medium per well of the 96-well microplates. HeLa cells were pre-incubated for 48 h prior to the addition of the test compounds (final DMSO concentration ≤0.5%), which were carefully diluted on the subconfluent monolayers. Incubation was then conducted in a humidified atmosphere at 37° C. and 5% $CO_2$. The adherent HeLa cells were fixed by glutaraldehyde and stained with a 0.05% solution of methylene blue for 10 min. After gently washing, the stain was eluted with 0.2 mL of 0.33 N HCl in the wells. The optical densities were measured at 660 nm in a SUNRISE microplate reader (TECAN).

Results of the afore-mentioned bioanalytical procedures are described in Table 1:

| Compound/ Example | MIC Mtb H37Rv [µg/ml] | MIC Mtb (PDR) 12700 [µg/ml] | MIC *M. marinum* [µg/ml] | MIC *M. vaccae* 10670 [µg/ml] | HeLa $CC_{50}$ [µg/mL] | Relative HMC formation [%] |
|---|---|---|---|---|---|---|
| 9a | 0.5 | 0.25 | 0.25 | 0.039 | 38.9 (±0.9) | <0.07 |
| 9b | 0.008 | 0.004 | 0.008 | <0.0012 | >50 | 5.26 |
| 16 | 0.0005 | ≤0.000063 | 0.001 | <0.0012 | >25 | <0.04 |
| PBTZ169 | n.d. | n.d. | n.d. | n.d. | n.d. | 80.7 |
| BTZ043 | 0.001 | 0.002 | 0.004 | <0.0012 | >50 | 100 |

PDR = Poly drug resistant (isoniazid and streptomycin); n.d. = not determined.

REFERENCES

1 Makarov, V., Manina, G., Mikusova, K., Möllmann, U., Ryabova, O., Saint-Joanis, B., Dhar, N., Pasca, M. R., Buroni, S., Lucarelli, A. P., Milano, A., De Rossi, E., Belanova, M., Bobovska, A., Dianiskova, P., Kordulakova, J., Sala, C., Fullam, E., Schneider, P., McKinney, J. D., Brodin, P., Christophe, T., Waddell, S., Butcher, P., Albrethsen, J., Rosenkrands, I., Brosch, R., Nandi, V., Bharath, S., Gaonkar, S., Shandil, R. K., Balasubramanian, V., Balganesh, T., Tyagi, S., Grosset, J., Riccardi, G. & Cole, S. T. Benzothiazinones Kill *Mycobacterium tuberculosis* by Blocking Arabinan Synthesis. Science 324, 801-804 (2009).

2 Zumla, A., Nahid, P. & Cole, S. T. Advances in the development of new tuberculosis drugs and treatment regimens. Nat. Rev. Drug Discov. 12, 388-404 (2013).

3 Makarov, V., Lechartier, B., Zhang, M., Neres, J., van der Sar, A. M., Raadsen, S. A., Hartkoorn, R. C., Ryabova, O. B., Vocat, A., Decosterd, L. A., Widmer, N., Buclin, T., Bitter, W., Andries, K., Pojer, F., Dyson, P. J. & Cole, S. T. Towards a new combination therapy for tuberculosis with next generation benzothiazinones. EMBO Mol. Med. 6, 372-383 (2014).

4 Tiwari, R., Möllmann, U., Cho, S., Franzblau, S. G., Miller, P. A. & Miller, M. J. Design and Syntheses of Anti-Tuberculosis Agents Inspired by BTZ043 Using a Scaffold Simplification Strategy. ACS Med. Chem. Lett, 5, 587-591 (2014).

5 Batt, S. M., Jabeen, T., Bhowruth, V., Quill, L., Lund, P. A., Eggeling, L., Alderwick, L. J., Fitterer, K. & Besra, G. S. Structural basis of inhibition of *Mycobacterium tuberculosis* DprE1 by benzothiazinone inhibitors. Proc. Natl. Acad. Sci. U.S.A. 109, 11354-11359 (2012).

6 Trefzer, C., Skovierova, H., Buroni, S., Bobovska, A., Nenci, S., Molteni, E., Pojer, F., Pasca, M. R., Makarov, V., Cole, S. T., Riccardi, G., Mikusova, K. & Johnsson, K. Benzothiazinones are suicide inhibitors of mycobacterial decaprenylphosphoryl-beta-D-ribofuranose 2'-oxidase DprE1. J. Am. Chem. Soc. 134, 912-915 (2012).

7 Neres, J., Pojer, F., Molteni, E., Chiarelli, L. R., Dhar, N., Boy-Röttger, S., Buroni, S., Fullam, E., Degiacomi, G., Lucarelli, A. P., Read, R. J., Zanoni, G., Edmondson, D. E., De Rossi, E., Pasca, M. R., McKinney, J. D., Dyson, P. J., Riccardi, G., Mattevi, A., Cole, S. T. & Binda, C. Structural Basis for Benzothiazinone-Mediated Killing of *Mycobacterium tuberculosis*. Sci. Trans. Med. 4, 150ra121-150ra121 (2012).

8 Anderson, J. C. & Koovits, P. J. An enantioselective tandem reduction/nitro-Mannich reaction of nitroalkenes using a simple thiourea organocatalyst. Chem. Sci. 4, 2897 (2013).

9 Khilyas, I. V., Ziganshin, A. M., Pannier, A. J. & Gerlach, R. Effect of ferrihydrite on 2,4,6-trinitrotoluene biotransformation by an aerobic yeast. Biodegradation 24, 631-644 (2013).

10 Tiwari, R., Moraski, G. C., Krchnak, V., Miller, P. A., Colon-Martinez, M., Herrero, E., Oliver, A. G. & Miller, M. J. Thiolates chemically induce redox activation of BTZ043 and related potent nitroaromatic anti-tuberculosis agents. J. Am. Chem. Soc. 135, 3539-3549 (2013).

11 Palomino, J. C., Martin, A., Camacho, M. et al. Resazurin microtiter assay plate: simple and inexpensive method for detection of drug resistance in *Mycobacterium tuberculosis*. Anticrob. Agents. Chemother. 46(8), 2720-2 (2002).

The invention claimed is:

1. A compound

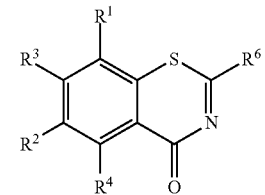

and/or a pharmaceutically acceptable salt thereof, selected from the group consisting of:
(S)-7-Methyl-2-(2-methyl-1,4-dioxa-8-azaspiro[4.5]decan-8-yl)-8-nitro-6-(trifluoromethyl)-4H-1,3-benzothiazin-4-one (9a),
(S)-5-Methyl-2-(2-methyl-1,4-dioxa-8-azaspiro[4.5]decan-8-yl)-8-nitro-6-(trifluoromethyl)-4H-1,3-benzothiazin-4-one (9b), and
2-(4-(Cyclohexylmethyl)piperazin-1-yl)-5-methyl-8-nitro-6-(trifluoromethyl)-4H-1,3-benzothiazin-4-one (16).

2. A compound selected from the group consisting of:
S)-5-Methyl-2-(2-methyl-1,4-dioxa-8-azaspiro[4.5]decan-8-yl)-8-nitro-6-(trifluoromethyl)-4H-1,3-benzothiazin-4-one (9b),
2-(4-(Cyclohexylmethyl)piperazin-1-yl)-5-methyl-8-nitro-6-(trifluoromethyl)-4H-1,3-benzothiazin-4-one (16) or a pharmaceutically acceptable salt thereof.

3. A pharmaceutical composition comprising a compound according to claim 1 and/or a pharmaceutically acceptable salt thereof.

4. A method for the therapeutic treatment of a mycobacterial infection in mammals comprising administering a therapeutically effective amount of a compound and/or a pharmaceutically acceptable salt thereof according to claim 1 to a patient in need thereof.

5. A method for the therapeutic treatment of tuberculosis or leprosy infection in mammals said method comprising administering a therapeutically effective amount of a compound and/or a pharmaceutically acceptable salt thereof according to claim 1 to a patient in need thereof.

6. A method for the therapeutic treatment of a mycobacterial infection in mammals comprising administering a therapeutically effective amount of a composition according to claim 3 to a patient in need thereof.

7. A method for the therapeutic treatment of tuberculosis or leprosy infection in mammals comprising administering a therapeutically effective amount of a composition thereof according to claim 6 to a patient in need thereof.

* * * * *